United States Patent [19]
Dime

[11] Patent Number: 5,621,106
[45] Date of Patent: Apr. 15, 1997

[54] METHOD OF MAKING IMMUNOSTIMULATING SWAINSONINE ANALOGS

[75] Inventor: David Dime, Toronto, Canada

[73] Assignee: Toronto Research Chemicals, Inc., Downsview, Canada

[21] Appl. No.: 456,764

[22] Filed: Jun. 1, 1995

Related U.S. Application Data

[60] Division of Ser. No. 232,231, Jul. 12, 1994, Pat. No. 5,466,809, filed as PCT/CA92/00479, Nov. 2, 1992, published as WO93/09117, May 13, 1993, which is a continuation-in-part of Ser. No. 788,583, Nov. 6, 1991, abandoned.

[51] Int. Cl.$^6$ ............................................. C07D 471/04
[52] U.S. Cl. ................................. 546/183; 536/17.3
[58] Field of Search ................................................ 546/183

[56] References Cited

PUBLICATIONS

Chemical Abstracts, vol. 106, No. 17, 27 Apr. 1987, abstract No. 138253y, S. Hashimoto et al., p. 673.
Chemistry Letters, No. 1, 1985, pp. 31–34, N. Yasuda et al., p. 33.
Tetrahedron, vol. 43, No. 13, 1987, pp. 3095–3108; G.N. Austin et al., pp. 3097, 3106.
Chemical Abstracts, vol. 104, No. 23, 9 Jun. 1986, abstract No. 207151, H. Tsutsumi et al, pp. 743–744, abstract.
Tetrahedron Letters, vol. 31, No. 2, 1990, pp. 169–170; W.A. Anderson et al, p. 170.
Tetrahedron Letters, vol. 3, No. 34, 18 Aug. 1992, pp. 4917–4920; Y. Chen et al. compound 2.
Copy of International Search Report prepared by the EPO as the ISA dated 02 Feb. 1993.

*Primary Examiner*—Bernard Dentz
*Attorney, Agent, or Firm*—Townsend and Townsend and Crew

[57] ABSTRACT

Immunostimulating derivatives of swainsonine and methods for their syntheses are disclosed.

6 Claims, 8 Drawing Sheets

ANALOGUES OF SWAINSONINE:

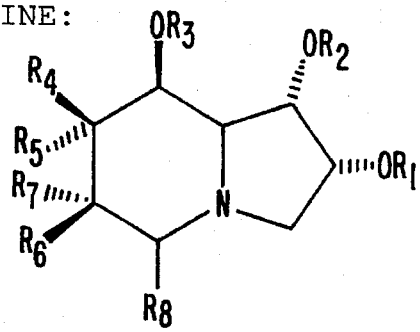

| ANALOGUE | | $R_1$ | $R_2$ | $R_3$ | $R_4$ | $R_5$ | $R_6$ | $R_7$ | $R_8$ |
|---|---|---|---|---|---|---|---|---|---|
| 1 | SWAINSONINE | H | H | H | H | H | H | H | $H_2$ |
| 4 | | $-Si(CH_C)_3$ | H | H | H | H | H | H | $H_2$ |
| 7 | | $-C(O)(CH_2)_2CO_2H$ | H | H | H | H | H | H | $H_2$ |
| 5 | | $-C(O)C_6H_5$ | H | H | H | H | H | H | $H_2$ |
| 41 | | $-p-C(O)C_6H_4CH_3$ | H | H | H | H | H | H | $H_2$ |
| 42 | | $-p-C(O)C_6H_4NO_2$ | H | H | H | H | H | H | $H_2$ |
| 6 | | $-C(O)(CH_2)_6CH_3$ | H | H | H | H | H | H | $H_2$ |
| 3 | | $-C(O)(CH_2)_2CH_3$ | H | H | H | H | H | H | $H_2$ |
| 12 | | H | H | H | ( | $-CH=CH-$ | | ) | =O |
| 13 | | Ac | Ac | Ac | ( | $-CH=CH-$ | | ) | =O |
| 23 | | H | H | H | (-OEH) | H | | H | =O |
| 25 | 7-ETHOXYSWAINSONINE | | | | | | | | |
| | | H | H | H | (-OEH) | H | | H | $H_2$ |
| 26 | | Ac | Ac | Ac | Br | H | H | OAc | =O |
| 27 | | Ac | Ac | Ac | H | Ac | Br | H | =O |
| 28 | | H | H | H | Br | H | H | OH | $H_2$ |
| 29 | | Ac | Ac | Ac | H | H | H | OAc | =O |
| 31 | | H | H | H | H | H | H | OH | $H_2$ |
| 30 | | Ac | Ac | Ac | H | OAc | H | Br | =O |
| 32 | | Ac | Ac | Ac | Br | H | H | Br | =O |
| 33 | | H | H | H | Br | H | H | H | $H_2$ |
| 34 | | Ac | Ac | Ac | -OH | H | -OH | H | =O |
| 35 | | Ac | Ac | Ac | -OAc | H | -OAc | H | =O |
| 36 | | H | H | H | -OH | H | -OH | H | $H_2$ |
| 37 | | H | H | H | H | H | H | H | =O |
| 38 | | H | H | H | H | H | H | H | OEl |
| 40 | | $-\beta-GlcNAc$ | H | H | H | H | H | H | $H_2$ |
| 39 | | $-\beta-GlcNAc(OAc)_3$ | H | H | H | H | H | H | $H_2$ |

*FIG. 3.*

3-AMINOMANNOSE     SWAINSONINE 1     4-AMINOMANNOSE

METHOD OF MAKING IMMUNOSTIMULATING SWAINSONINE ANALOGS

This is a division of U.S. application Ser. No. 08/232,231, filed Jul. 12, 1994, which application is now U.S. Pat. No. 5,466,809 which was a 371 of PCT/CA92/00479 filed Nov. 7, 1992 published as WO93/09117, May 13, 1993, which was a continuation-in-part of application Ser. No. 07/788,583, which was filed on Nov. 6, 1991, which application was abandoned.

FIELD OF THE INVENTION

The invention relates to processes for the production of swainsonine analogs known in general terms as indolizidine compounds and products thereof.

BACKGROUND OF THE INVENTION

Swainsonine, 1, (the general structure of which is presented in FIG. 1) is an alkaloid of molecular weight 173.1 which may be derived from both natural and synthetic sources. Swainsonine is a competitive inhibitor of Golgi alpha-mannosidase II (Molyneux, R. J. et al., Science (Wash. DC) 216: 190 (1981); Tulsiani, D. R. P. et al., J. Biol. Chem. 257: 7936 (1982)), an enzyme important in the oligosaccharide processing pathway leading to the synthesis of complex membrane oligosaccharides and secreted glycoproteins. This action, as well as the immunomodulatory effects of swainsonine, accounts in part for antimetastatic and antineoplastic activity in murine tumor model systems. Swainsonine has also been shown to mediate a diverse array of effects, which include inhibition of tumor growth (Dennis et al., J. Nat'l. Cancer Inst., 81: 1028 (1989)) and metastasis (White et al., Anticancer Res., 10: 1515 (1990)), synergistic with poly-IC and interleukin-2 (J. W. Dennis, Mt. Sinai Hospital, European Patent Application 87308605.2); augmentation of natural killer (Inamura et al., J. Antiblot. Tokyo, 38: 936 (1985)) and macrophage (Newton et al., Cancer Commun., 1: 373 (1989)) tumoricidal activity; induction of cytokine synthesis and secretion (Newton et al., Cancer Commun., 1: 373 (1989)); enhancement in expression of lak (Newton et al., Cancer Commun., 1: 373 (1989)) and HLA class 1 specific antigens (White et al., Anticancer Res., 10: 1515 (1990)); activation of protein kinase C (Breton et al., Cancer Commun., 2: 333 (1990)); stimulation (5–10 fold increase) of bone marrow (BM) proliferation (Whine et al., Cancer Commun., 3: 83 (1991)); engraftment efficiency, and colony-forming unit activity (CFU-GM, CFU-GEMM, and BFU-E) as assessed by both in vivo and in vitro assays. Swainsonine has also been shown to confer Protection against toxicity induced by high dose chemotherapy, no stimulate BM cell proliferation, and no accelerate recovery of BM cellularity when used in combination with chemical agents commonly used in treatment of human malignancies, (J. Nat. Cancer Inst., 83: 1125, 1991). Published European Patent Application 0 104 826 also discloses swainsonine; moreover, it indicates therapeutic dosages and how they are determined for use in treating diseases accompanied by depressed immunoactivity.

Swainsonine offers a number of advantages over recombinant growth factors and cytokines. It is possible that swainsonine induces the simultaneous paracrine production, in modest quantities, of a number of cytokines. This effect may allow marrow protection in the absence of toxicity and the complexities involved in administration of one or more growth factors to an individual. In addition, swainsonine has biological activity when administered orally. Therefore, the potential exists for a convenient route of administration of swainsonine which is not possible using recombinant proteins. Furthermore, the simplicity of the molecule may facilitate inexpensive production of a suitable formulation.

With regard to the synthesis of (–)-swainsonine, several enantioselective syntheses of the natural alkaloid have been reported. Many of these utilize carbohydrates as chiral precursors. Syntheses from D-mannose [Gonzales et. al., Bull. Chem. Soc. Jpn., 65: 567 (1992); T. Takaya et. al., Chem. Lent., 1201 (1984); G. W. J. Fleet et al., Tet. Lett., 25: 1853 (1984); G. W. J. Fleet et al., Tetrahedron, 43: 3083 (1987); G. W. J. Fleet en al., Tet. Lett. 30: 7261 (1989)], D-glucose [A. C. Richardson et al., Carb. Res. 136: 225 (1985); A. C. Richardson et al., J. Chem. Soc., Chem. Comm. 447 (1984); T. Saumi et al., Chem. Lett. 513 (1984); T. Saumi et al., Carb. Res., 136: 67 (1985) )], D-erythrose [J. K. Cha et al., J. Amer. Chem. Soc., 111: 2580 (1989); W. H. Pearson, Tet. Lett., 52: 7571 (1990)], D-xlyxose [A. R. Chamberlain, J.Amer. Chem. Soc., 112: 8100 (1990)], D-ribonolactone [N. Ikota et al., Chem. Pharm. Bull., 36: 1143 (1988)], glutamic acid [N. Ikota et al., Chem. Pharm. Bull., 35: 2140 (1987); N. Ikota et al., Chem. Pharm. Bull. 38.2712 (1990); D-tartaric acid [D.J. Hart et al., J. Org. Chem., 53: 6023 (1988)] have all been reported. The synthesis of (–)-swainsonine has also been reported starting from achiral precursors. K. B. Sharpless [K. B. Sharpless et al., J. Org. Chem., 50: 422 (1985)] reported a 21 step synthesis starting from trans-1,4-dichloro-2-butene employing the methodology of the Masamune/Sharpless iterative approach to polyhydroxylated natural products [S. Masamune, K. B. Sharpless et al., J. Org. Chem., 47: 1373 (1982), Science, 220: 949 (1983)].

Castanospermine, 2, 1S-8a-beta-octahydroindolizine-1-alpha-6-beta-7-alpha-8-beta-tetraol (see Formula 2 below) an inhibitor of the endoplasmic reticulum enzyme alpha-glucosidase, has been converted specifically to mono- and di-O-acylated derivatives (P. S. Liu et al., Tet. Lett, 32: 719 (1991); P. S. Liu et al., Tet. Lett., 31: 2829 (1990); A. L. Margolin et al., J. Amer. Chem. Soc., 112: 2850 (1990): W. K. Anderson et al., Tet. Lett., 31: 169 (1990)). It has been reported that several O-acyl derivatives castanospermine are as much as 20 times more active than castanospermine itself in inhibiting HIV replication (P. S. Sunkara et al., The Lancet, 1206 (1989)). The structure of castanospermine is illustrated in FIG. 2.

The lipophilicity of a hydrophilic drug can enhance absorption from the GI tract and alter the organ distribution. Rall et al., (in Ann. Rev. Pharm., 2: 109 (1962)), have reported that small lipophilic molecules cross the blood-brain barrier more efficiently than large ones. Esters of hydrophilic drugs may be cleaved by enzymes in the blood stream releasing the free drug, thus the profile of excretion may also be affected by the structure of these derivatives. An example of this is acetylsalicylic acid, which is cleaved to the active agent, salicylic acid, in the liver and in various other tissues (D. Lednicer et al., The Organic Chemistry of Drug Synthesis, J. Wiley and Sons, Vol. 1, pg. 108, 1977).

A number of acyl derivatives of swainsonine have been synthesized. In the course of the initial structure determination of swainsonine, acetylation of swainsonine with acetic anhydride at room temperature was found to yield a 1,2-diacetate derivative (S. M. Colegate et al., Aust. J. Chem., 32: 2257 (1979)). Researchers at Fujisawa Pharmaceutical Co., Ltd. have also prepared a number of acylated derivatives of swainsonine as immunomodulators (Jpn. Kokai Tokkyo Koho 61,277685). These compounds include tri-O-acylated derivatives of swainsonine, 1, 2-di-O-acetylated derivatives of swainsonine, 1, 8-di-O-benzoyl swainsonine and 2, 8-di-O-benzoyl swainsonine and 8-O-acylated derivatives. Other acetylated derivatives of swainsonine reported in the chemical literature arise as intermediates in various syntheses of swainsonine. These are tri-O-acylated compounds.

Because swainsonine contains three similar hydroxyl functions (see FIG. 1), direct modification of swainsonine by manipulation of these hydroxyl groups represents a formidable synthetic challenge. Japanese Kokai Tokyo Koho 61,277685 discloses the difficulty in differentiating between the 1 and 2 hydroxyl groups of swainsonine.

The reaction of 1, 2-diols with dibutyltin oxide results in the formation of a cyclic 5-membered dibutylstannyl derivative. These have been successfully used in carbohydrate and nucleoside chemistry (D. Wagner et al., J. Org. Chem., 39: 24 (1974)) as a protecting group or as an activating group for subsequent alkylations, acylations and oxidations (Chem. Pharm. Bull., 37: 2344 (1989)).

Other than the initially reported conversion of swainsonine to its 1, 2-di-O-acetyl derivative, site specific acylation of swainsonine is not known to have been reported to date.

The reaction of diols with dibutyltin oxide is known to form a cyclic dibutylstannane derivative which can function as both a protecting group, or be utilized to activate one of the hydroxyl groups toward alkylation, acylation (J. Org. Chem. 39: 24 (1974)), or even oxidation (Chem. Pharm. Bull, 2344 (1989)). This technique has been utilized in carbohydrate, and nucleotide chemistry where the diol is part of a molecule containing other hydroxyl groups. It was also utilized to prepare esters of castanospermine (Tetrahedron Letters, 169 (1990).

The glycosylation of tin alkoxides was reported in 1976 [Carbohydrate Res. 51: C13 (1976)]. The reaction of acetobromoglucose with the tributyltin salts of various alcohols, in 1,2-dichloroethane was catalyzed with tin tetrachloride. These reactions afforded reasonable yields of the glycosides. When the reaction is run with tetraethylammonium bromide, orthoesters are produced. The conversion of such orthoesters into 1,2-trans-glycosides is well established [Kochetkov et. al., Tetrahedron 23: 693 (1967); Zurabyan et. al. Carbohydrate Res. 26: 117 (1973); T. Ogawa et. al., Tetrahedron 37: 2779 (1981); T. Ogawa et. al., Tetrahedron 37: 2787(1981)]. These papers deal with the glycosylation of the salts produced by reaction of trialkyltin enolates with glycosyl halides.

Glycosyl donors are commonly carbohydrates activated for coupling to hydroxyl groups. This includes activation as the glycosyl bromide, chloride, fluoride, tosyl, or oxazoline compound or activation via imidate chemistry [B. Wegmann et. al., J. Carb. Chem., 357: (1987); R. R. Schmidt, Tet. Lett. 32: 3353 (1991)] or as a thioglycoside [J. O. Kihlberg, et. al. J. Org. Chem. 55, 2860 (1990)], and cited references)]. The reaction of glycosyl donors with hydroxyl groups to afford glycosides is normally promoted utilizing silver salts, mercury salts, trifluoromethanesulfonic anhydride [H. P. Wessel, Tet. Lett. 31: 6863 (1990)].

BRIEF DESCRIPTION

A swainsonine compound of the formula depicted in FIG. 1 or a salt of said compound, where R is selected from the group consisting of C=O $(CH_2)_2CH_3$, $Si(CH_3)_3$, C=$OC_6H_5$, C=$O(CH_2)_6CH_3$, C=$O(CH_2)_2COOH$, $Si(C_6H_5)_2C(CH_3)_3$, $Si(CH_3)_2C(CH_3)_3$, C=$O(CH_2)_{16}CH_3$, C=$O(CH_2)_{14}CH_3$, C=$O(CH_2)_{12}CH_3$, C=$OC_6H_5$, 2-furoyl, m-toluoyl, p-nitrobenzoyl, p-toluoyl, p-bromobenzoyl, p-nitrobenzoyl, p-toluenesulfonyl, methanesulfonyl, ethanesulfonyl, propanesulfonyl, isopropanesulfonyl, butanesulfonyl, benzyl, allyl, 4-methoxytrityl, triphenylmethyl, butyl, pentyl, hexyl, heptyl, octyl, dodecyl, hexadecyl, octadecyl, acetyl, propionyl, pivaloyl, phenoxypropionyl, imadazolyl, imadazoylthiocarbonyl, 2,3,4,6-tetra-O-acetyl-β-D-glucopyranosyl, β-D-glucopyranosyl, 2,3,4,6-tetra-O-acetyl-alpha-D-mannopyranosyl, alpha-D-mannopyranosyl, 2,3,4,6-tetra-O-acetyl-β-D-mannopyranosyl, β-D-mannopyranosyl, 2-acetamido-2-deoxy-3,4,6-tri-O-acetyl-β-D-glucopyranosyl, 2-acetamido-2-deoxy-β-D-glucopyranosyl, 2,3,4-tri-O-benzyl-alpha-L-fucopyranosyl, alpha-L-fucopyranosyl, 2,3,4,6-tetra-O-acetyl-β-D-galactopyranosyl, β-D-galactopyranosyl, 2-acetamido-2-deoxy-3,4,6-tri-O-acetyl-β-D-galactopyranosyl, 2-acetamido-2-deoxy-β-D-galactopyranosyl, 2-acetamido-2-deoxy-3,4,6-tri-O-acetyl-alpha-D-galactopyranosyl, 2-acetamido-2-deoxy-alpha-D-galactopyranosyl, N-acetylneuraminyl, lactosaminyl, β-D-glucuronyl, and the like, and methods of making the same.

A swainsonine compound of the formula depicted in FIG. 3, and methods of making the same.

DETAILED DESCRIPTION OF THE INVENTION

The drawings will first be described.

The Drawing:

FIG. 3 is a more general formula for swainsonine.

METHODS AND PRODUCTS

Figure 1:
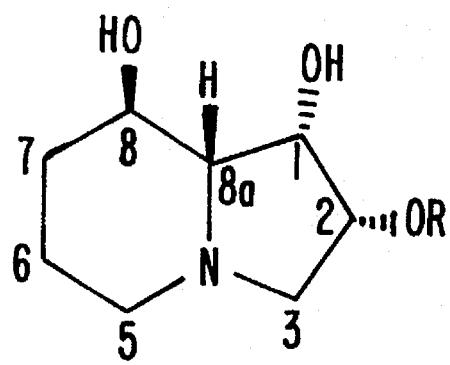
FIG. 1 is the general formula for swainsonine and its analogs.
Figure 2:
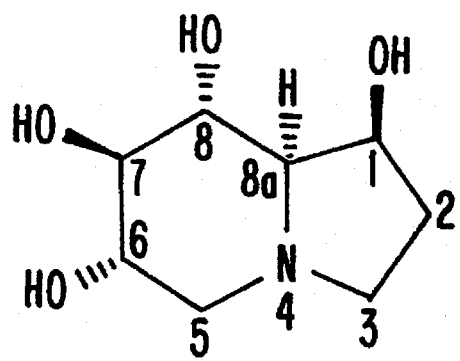
FIG. 2 is the general formula for castanospermine.
Figure 4:
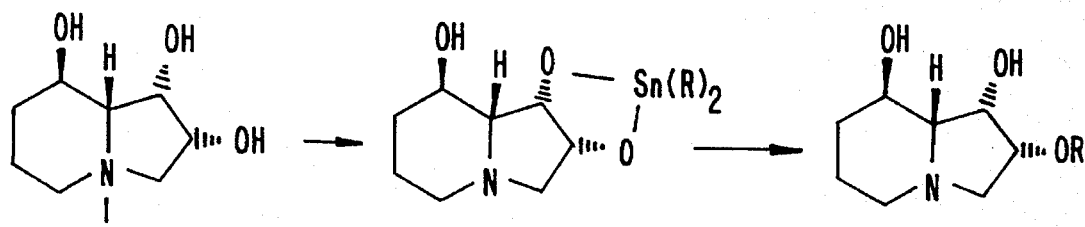
FIG. 4 is scheme for a general method for the production of 2-O-derivatized swainsonine.
Figure 5:
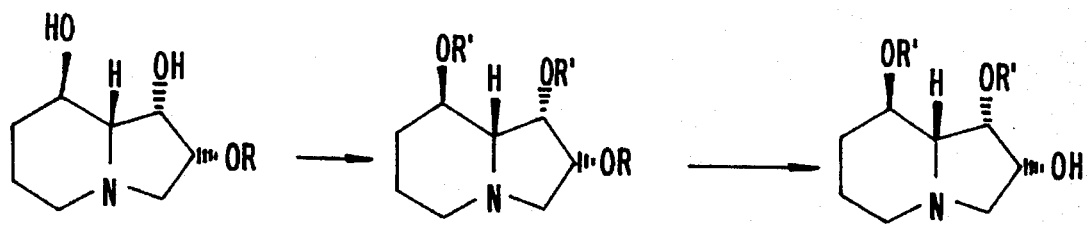
FIG. 5 is scheme for a general method for the synthesis of swainsonine analogs using a protecting agent.

This invention includes a one-pot method to convert swainsonine, 1S-8a-beta-octahydro-indolizine-1 alpha-2 alpha-8 β-triol, to its specifically 2-O-derivatized analogs. These compounds are analogs of swainsonine. Their composition is presented in FIG. 1.

Where R is selected from the group consisting of $C{=}O(CH_2)_2CH_3$, $Si(CH_3)_3$, $C{=}OC_6H_5$, $C{=}O(CH_2)_6CH_3$, $C{=}O(CH_2)_2COOH$, $Si(C_6H_5)_2C(CH_3)_3$, $Si(CH_3)_2C(CH_3)_3$, $C{=}O(CH_2)_{16}CH_3$, $C{=}O(CH_2)_{14}CH_3$, $C{=}O(CH_2)_{12}CH_3$, 2-furoyl, m-toluoyl, p-toluoyl, p-nitrobenzoyl, p-bromobenzoyl, p-toluenesulfonyl, methanesulfonyl, ethanesulfonyl, propanesulfonyl, isopropanesulfonyl, butanesulfonyl, benzyl, allyl, 4-methoxytrityl, triphenylmethyl, butyl, pentyl, hexyl, heptyl, octyl, dodecyl, hexadecyl, octadecyl, acetyl, propionyl, pivaloyl, phenoxypropionyl, imadazolyl, imadazoylthiocarbonyl, 2,3,4,6-tetra-O-acetyl-β-D-glucopyranosyl, β-D-glucopyranosyl, 2,3,4,6-tetra-O-acetyl-alpha-D-mannopyranosyl, alpha-D-mannopyranosyl, 2,3,4,6-tetra-O-acetyl-β-D-mannopyranosyl, β-D-mannopyranosyl, 2-acetamido-2-deoxy-3,4,6-tri-O-acetyl-β-D-glucopyranosyl, 2-acetamido-2-deoxy-β-D-glucopyranosyl, 2,3,4-tri-O-benzyl-alpha-L-fucopyranosyl, alpha-L-fucopyranosyl, 2,3,4,6-tetra-O-acetyl-β-D-galactopyranosyl, β-D-galactopyranosyl, 2-acetamido-2-deoxy-3,4,6-tri-O-acetyl-β-D-galactopyranosyl, 2-acetamido-2-deoxy-β-D-galactopyranosyl, 2-acetamido-2-deoxy-3,4,6-tri-O-acetyl-alpha-D-galactopyranosyl, 2-acetamido-2-deoxy-alpha-D-galactopyranosyl, N-acetylneuraminyl, lactosaminyl and β-D-glucuronyl.

The compounds of FIG. 1 may be swainsonine (when R is H), ester, ether or protected derivatives of swainsonine or their salts.

Examples of pharmaceutically acceptable salts of swainsonine derivatives include an acid addition salt at the $N_4$ position with an organic acid selected from maleic acid, fumaric acid, tartaric acid, acetic acid, benzoic acid and the lake or an inorganic acid selected from methane sulfonic acid, hydrochloric acid, hydrobromic acid, sulfuric acid, nitric acid, phosphoric acid and the like.

The swainsonine analogs of the instant invention are expected to exhibit immunostimulating properties including but not limited to restoration of depressed immunity and stimulation of bone marrow cells. Thus, these analogs should be useful in the therapeutic treatment of diseases which demonstrate a depression of immunoactivity.

Diseases which may be treated with the swainsonine analogs of the instant invention include tumors, infectious diseases, allergies, autoimmune diseases and the like. The analogs of the present invention may be delivered by injection or by mouth.

The analogs may be used alone or in conjunction with agents including but not limited to the complex of polyinocinic and polycytidylic acid (poly-IC) and interleukin-2 which increase their anticancer effects. Whether used alone or with another agent, a pharmaceutical composition comprising a therapeutically effective amount of the analog of the instant invention is combined with a carrier for delivery.

It is contemplated that these compounds retain or surpass the anticancer, antiviral and immuno-stimulating effects, including colony stimulating effects, of swainsonine, due to increased absorption and/or selective organ distribution. The esters are possibly pro-drugs which are converted to swainsonine by enzymes in vivo. They are also believed to have biological activity of their own.

It is within the ordinary skill in the art to determine therapeutic dosage requirements of the instant swainsonine analogs based on in vitro studies, in vivo studies including patient weight and drug concentration.

The swainsonine analogs of the invention are also useful as intermediates for making additional analogs with pharmaceutical potential.

GENERAL METHOD OF MAKING ANALOGS

Differentiation between 1,2 and 8 hydroxyl groups of swainsonine is achieved by utilizing tin chemistry.

Swainsonine is treated with dibutyltin oxide, or other tin oxides, in an appropriate solvent such as methylene chloride chloroform, toluene, methanol and the like. The resulting cyclic tin derivative is reacted, in situ, with an acylating agent, alkylating agent or protecting agent to specifically produce the 2-O-derivatized swainsonine. The scheme depicting these reactions is illustrated in FIG. 4.

When a protecting agent is utilized, the 2-protected product may be further reacted. Protecting agents include benzyl chloride, allyl chloride, triphenylmethyl chloride, 4-methoxytrityl chloride and silyl chlorides such as chlorotrimethylsilane, t-butylchlorodimethylsilane, t-butyldiphenylchlorosilane and the like. The swainsonine analogs of the current invention include such protected derivatives of swainsonine. In the case where a protecting group is utilized, the 1 and 8 hydroxyl groups of the protected compound may be derivatized by aklylation, acylation, or with a protecting agent. The protecting groups may be subsequently removed by hydrolysis or hydrogenolysis for example. The scheme depicting these reactions is illustrated in FIG. 5.

For purposes of the claimed invention, the term "acyl" includes aliphatic acyl groups, aromatic and heterocyclic acyl groups.

The acylating agents used in this synthesis method include but are not limited to activated carboxylic acids, including acid halides, acid anhydrides, activated amides, activated esters, sulfonic acid esters (including toluenesulfonyl, methanesulfonyl, ethanesulfonyl, propanesulfonyl, isopropanesulfonyl, butanesulfonyl), fatty acid groups (including acetyl, propionyl, t-butyl, myristoyl, palmitoyl, stearoyl), aromatic acyl groups (including benzoyl, toluoyl, phenoxypropionyl) heterocyclic acyl groups, which are cyclic groups containing one or more atoms of N, O or S (including furoyl, imidazolyl, imidazolylthiocarbonyl compounds) and the like.

Alkylating agents include, but are not limited alkyl (methyl, ethyl, propyl, butyl, pentyl, hexyl, heptyl, octyl, dodecyl, hexadecyl and octadecyl) halides and the like.

Glycosyl donors are also encompassed within the class of alkylating agents. This group of compounds includes, but is not limited to acetobromoglucose, acetobromomannose, acetobromogalactose, acetobromofucose, methyl acetobromogulcuronide, methyl acetochloroneuraminic acid, acetochloro-2-acetamido-2-deoxyglucopyranoside, acetochlorolactosamine, and the like.

Reactions may be performed while cooling, at room temperature, or while heating, but generally require fairly mild conditions.

Structural assignments of the swainsonine analogs were made by $^1$H NMR spectral analysis. The spectra of the derivatized swainsonine compounds were compared to that of the swainsonine. Peak assignments made on the basis of COSY 2-D NMR $^1$H connectivities. (See Table 1).

TABLE 1

| | $^1$H Chemical Shifts at 500.135 MHz | |
|---|---|---|
| Proton | Swainsonine[a] | 1S-8a-β-2-alpha-octanoyloxy-octahydroindolizine-1-alpha-8-β-diol[c] |
| 1 | 4.414 | 4.406[b] | 4.332 |
| 2 | 4.217 | 4.200 | 4.922 |
| 3 cis[c] | 2.176 | | 2.873 |
| 3 trans[c] | 3.116 | | 2.044 |
| 5a[d] | 1.678 | | 1.471 |
| 5e[d] | 2.754 | | 2.554 |
| 6a | 1.582 | | 1.35[f] |
| 6e | 1.439 | | 1.28[f] |
| 7a | 1.350 | | 1.079 |
| 7e | 2.136 | | 1.861 |
| 8 | 4.107 | 4.110 | 3.728 |
| 8a | 1.740 | | 1.462 |
| 1-OH | 4.737 | | |
| 2-OH | 4.509 | | |
| 8-OH | 4.244 | | |

[a]Solvent: $C_6D_6$ + 2 drops DMSO-$D_6$
[b]Solvent: $C_6D_6$ + drops DMSO-$D_6$ + 1 drop $D_2O$
[c]3 cis refers to H-3 cis to H-2 and 3 trans refers to H-3 trans to H-2
[d]"a" indicates an axial proton while "e" indicates an equatorial proton
[e]Solvent $C_6D_6$
[f]Partially overlapped with $(CH_2)_6$ proton signals

EXAMPLE 1

1S-8a-β-2-alpha-butanoyloxy-octahydroindoliziue-1-alpha-8-β-diol. 3 Swainsonine (1S-8a-β-octahydroindolizine-1-alpha-2-alpha-8-β-triol), 0.050 g (0.00029 mole) and 0.080 g (0.00032 mole) dibutyltin oxide, 0.2 g 3A molecular sieves, and 15 ml chloroform were heated at reflux under argon overnight. The reaction mixture was allowed to cool to room temperature, and 0.034 ml (0.00032 mole) butyryl chloride was added by syringe. The mixture was stirred at room temperature overnight. Following filtration and evaporation, the mixture was purified by chromatography on silica gel. The Product, 1S-8a-β-2-alpha-butanoyloxyoctahydroindolizine-1-alpha-8-β-diol, 3, was eluted with chloroform methanol as a crystalline solid upon evaporation of the solvent. This was taken up in ether-hexane and filtered to afford 0.020 g product, which was recrystallized from ether to afford white needles having a melting point (top) of 103°–104° C.

$^1$H NMR (500 Mhz, $C_6D_6$ delta): 4.91–4.88 (1H; m, H-2); 4.32 (1H; brs, H-1); 3.75–3.70 (1H; m, H-8); 2.85 (1H; dd, J=1.8 Hz, 10.6 Hz); 2.55 (1H; brd, J=10.6 Hz); 2.13–1.04 (13H; complex) 1 0.80 (3H; t, J=7.4 Hz)

EXAMPLE 2

1S-8a-β-2-alpha-trimethylsilyloxy-octahydroindolizine-1-alpha-8-β-diol. Swainsonine (1S-8a-β-octahydroindolizine-1-alpha-2-alpha-8-β-triol), 0.100 g (0.00058 mole), 0.160 g (0.00064 mole) dibutyltin oxide, 0.2 g 3A molecular sieves, and 15 ml chloroform were heated at reflux under argon overnight. The reaction mixture was allowed to cool to room temperature, and 0.092 ml (0.078 g, 0007266 mole) chlorotrimethyl silane was added by syringe. The mixture was stirred at room temperature overnight; then filtered, evaporated, and purified by chromatography on silica gel. The product, 1S-8a-β-2-alpha-trimethylsilyloxyoctahydroindolizine-1-alpha-8-β-diol, was eluted with chloroform methanol as-a crystalline solid upon evaporation of the solvent. This was taken up in etherhexane and filtered to afford 0.020 g product mp 122°–124° C.

$^1$H NMR (500 Mhz, $C_6D_6$-DMSO-D6 delta): 4.28–4.26 (1H; m); 4.15–4.11 (2H; m); 4.02–3.99 (1H; m); 3.17 (1H; d, J=6.5 Hz); 2.86 (1H; dd, J=1.4 Hz, 9.8 Hz); 2.72 (1H; brd, J=10.7 Hz); 2.16–2.11 (2H; complex) 1.75–1.31 (5H; complex); 0.06 (9H; s)

EXAMPLE 3

1S-8a-β-2-alpha benzoyloxyoctahydroindolizine-1-alpha-8-B-diol. 5. Swainsonine (1S-8a-β-octahydroindolizine-1-alpha-2-alpha-8-β-triol), 0.100 g (0.00058 mole) and 0.160 g (0.00064 mole) dibutyltin oxide were heated at reflux in methanol (10 ml) under argon for 2 hours. The reaction mixture was cooled to room temperature, and triethylamine (0.293g, 0.0029065 mole; 5 molar equivalents) was added followed by benzoyl chloride 0.34 ml (0.408 g; 0.0029065 mole; 5 molar equivalents). The mixture was stirred at room temperature overnight, filtered and evaporated. The residue was purified by flash chromatography on silica gel (10 g). The product 1S-8a-β-2-alpha-benzoyloxyoctahydroindolizine-1-alpha-8-β-diol, 5, was eluted with methylene chloride-methanol (24: 1). The solvent was evaporated and the residue 0.050 g was recrystallized from ether to yield white needles of mp 158°–159° C.

$^1$H NMR (500 Mhz, $C_6D_6$-DMSO-D6 delta): 8.22 (2H; aromatic); 7.09 (3H; aromatic); 5.29–5.26 (1H; m, H-2); 4.77–4.74 (1H; m); 4.51 (1H; d, J=4 Hz); 4.11–4.06 (1H; m); 4.04 (1H; d, J=7.6 Hz); 3.15 (1H; dd, J=1.9 Hz, 10.6 Hz); 2.74 (1H; brd, J=10.4 Hz); 2.28 (1H; dd, J=8 Hz, 10.5 Hz); 2.14–2.11 (1H; m) 1.82 (1H; dd, J=3.8 Hz, 8.7 Hz); 1.71–1.13 (4H; complex)

EXAMPLE 4

1S-8a-β-2-alpha-octanoyloxyoctahydroindolizine-1-alpha-8-β-diol. 6. Swainsonine (1S-8a-β-octahydroindolizine-1-alpha-2-alpha-8-β-triol), 0.100 g (0.00058 mole) and 0.160 g (0.00064 mole) dibutyltin oxide were heated at reflux in methanol (10 ml) under argon for 2 hours. The reaction mixture was cooled to room temperature, and triethylamine (0.293 g, 0.0029065 mole; 5 molar equivalents) was added followed by octanoyl chloride 0.5ml (0.47 g; 0.0029065mole; 5 molar equivalents). The mixture was stirred at room temperature overnight, filtered and evaporated. The residue was purified by flash chromatography on silica gel (10 g). The product 1S-8a-β-2-alpha-octanoyloxy-octahydroindolizine-1-alpha-8-β-diol, 6, was eluted with methylene chloride-methanol (24: 1). The solvent was evaporated and the residue was taken up in ether-hexane and filtered to afford 0.055 g white crystalline solid, mp 103°–104° C.

$^1$H NMR (500 Mhz, $C_6D_6$ delta): 4.92 (1H; m, H-2); 4.33 (1H; m, H-1); 3.73 (1H; m, H-8); 2.87 (1H; dd, J=2 Hz, 10.6 Hz, H-3 cis to H-2); 2.55 (1H; dr, J=3.2 Hz, 10.6 Hz, H-5 eq.); 2.23–2.13 (2H; m); 2.04 (1H; dd, J=7.6 Hz, 10.6 Hz, H-3 trans to H-2); 1.99 (1H; brd, J=10.6 Hz); 1.86 (1H; m, H-7 eq.); 1.74 (1H; brs); 1.62–1.56 (2H; complex); 1.40–1.16 (1 OH; complex); 1.12–1.04 (1H; m, H-7 ax.); 0.86 (3H; t, J=7 Hz, CH$_3$).

EXAMPLE 5

1S-8a-β-2-alpha-succinyloxyoctahydroindolizine-1-alpha-β-diol. 7. Swainsonine (1S-8a-β-octahydroindolizine-1-alpha-2-alpha-8-β-triol), 0.100 g (0.00058 mole) and 0.160 g (0.00064 mole) dibutyltin oxide, 0.2 g 3 Å molecular sieves, and 15 ml chloroform was heated at reflux under argon overnight. The reaction mixture was allowed to cool to room temperature, and 0.072 g (0.0007225 mole) succinic anhydride was added. The mixture was stirred at room temperature overnight. It was then filtered, evaporated, and purified by chromatography on a silica gel. The product, was eluted with methanol and the solvent evaporated. The residue was taken up in methanol and acetic acid was added. The solvent was evaporated and the residue began to solidify upon standing overnight. The product was taken up in ethanol and filtered to afford 1S-8a-β-2-alpha-succinyloxy-octahydroindolizine-1-alpha-8-β-diol, 7, 60 mg (0.00022 mole; 38%) as a white crystalline solid, mp 122°–124° C.

Figure 6:
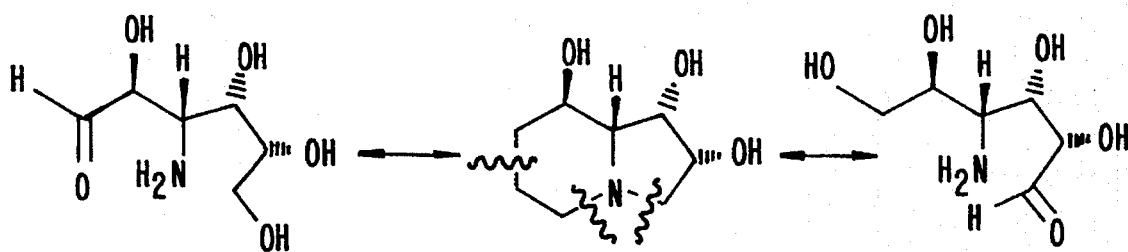
FIG. 6 is a general scheme for synthesis of swainsonine from a carbohydrate precursor.

The Synthesis of Swainsonine Via Intramolecular Horner Emmons, Wittig Type Reaction The synthesis of Swainsonine from a carbohydrate precursor, can be viewed as arising from either a 4-aminomannose, or a 3-aminomannose structure depicted in FIG. 6.

The invention includes an intramolecular Wittig Route to Swainsonine from 3-aminomannose derivatives. In the Wittig reaction, an aldehyde or ketone is treated with a phosphorous ylide (also called a phosphorane) to yield an olefin. The Wittig reaction can be carried out with other types of ylides, the most important being those prepared from phosphonates. This method, termed the Horner-Emmons or Wadsworth-Emmons reaction affords ylides that are more reactive than the corresponding phosphoranes. The phosphoranes are available from the Arbozov reaction of a trialkylphosphite with an alkyl halide [J. March, "Advanced Organic Chemistry", Third Edition, J. Wiley and Sons, p.845–854, 1985, and references therein].

The route to Swainsonine from 3-aminomannose and other 3-aminosugar derivatives can proceed by two pathways. The first involves the formation of the 5-membered ring by the displacement of a leaving group at the C-6 position of the original mannose derivative [A. G. Richardson et. al., Carb. Res. 136: 225 (1985)]. In the second pathway, the 6-membered ring joining the C-1 position of the 3-aminomannose derivative to the 3-amino group is fabricated first, and the 5-membered ring later. By utilizing both schemes, and 3-aminosugars other than mannose, it is possible to produce a vast array of indolizidine final products containing different substituents and stereochemistry to that of Swainsonine. By not completing the formation of the second ring, pyrrolidines and piperidines may be produced. An intramolecular Wittig has not yet been employed in the synthesis of Swainsonine.

The route to Swainsonine can proceed by two pathways. In the first, the initial step involves fabrication of the 5-membered ring. Methyl 3-amino-3-deoxymannopyranoside, is prepared by the periodate oxidation of methyl glucopyranoside subsequent condensation with nitromethane and reduction of the nitro compound produced [A. G. Richardson, J. Chem. Soc., 373 (1962)]. This compound is converted, in high yield, to methyl 3,6-dideoxyimino-alpha-D-mannopyranoside, 8 [A. G. Richardson et. al., Carb. Res. 136: 225 (1985)]. The invention includes an extension of this methodology to other glucosides to utilize these compounds for the synthesis of swainsonine and its analogues.

EXAMPLE 6

Summary of the Synthesis of Swainsonine from Methyl 3,6-dideoxyimino-alpha-D-mannopyranoside. Methyl 3,6-dideoxyimino-alpha-D-mannopyranoside, 8, [A. G. Richardson et. al., Carb. Res. 136: 225 (1985)], was treated with chloroacetic anhydride, or chloroacetyl chloride to afford the chloroacetamido derivative 9. The anomeric methyl group was cleaved by acetolysis to give 10. Arbuzov reaction [see A. K. Bhattacharya et al., Chem. Rev., 81: 415 (1981)], with triethylphosphite yielded 11, and subsequent treatment with base led to intramolecular Horner-Emmons, Wittig type cyclization (see Yu. A. Zhdanov et. al., Adv. in Carb. Chem., 27: 227 (1972), P. Vogel et. al., J. Org. Chem., 56: 2128 (1991)) to afford the enamide 12. Acetylation, to give 13, and subsequent reduction of the double bond yielded (1S, 2R,8R,8aR)-1,2,8- triacetoxy-5-oxo-octahydroindolizine 14. The physical constants agreed with those of Richardson [A. C. Richardson et. al., Carb. Res., 136: 225 (1985)], wherein this compound was prepared by a different route. Compound 14 may be converted to swainsonine in good yield [A. C. Richardson et. al., Carb. Res., 136: 225 (1985)] by reduction of the amide using borane-dimethylsulfide complex, followed by deacetylation.

The Arbuzov reaction could either preceed the cleavage of the anomeric protecting group, or, alternatively, conversion to the phosphonate could be effected after cleavage of the anomeric protecting group.

The Arbuzov reaction of 9, or 10 could be effected either with a trialkylphosphite alone at about 100°–120°C., or with a catalyst such as a tetraalkylammonium iodide salt, at about 40°–50°C., or alternatively, by conversion of the chloroacetamide to the iodoacetamide, and in a subsequent step reaction of the iodocompound with a trialkylphosphite.

Figure 7:
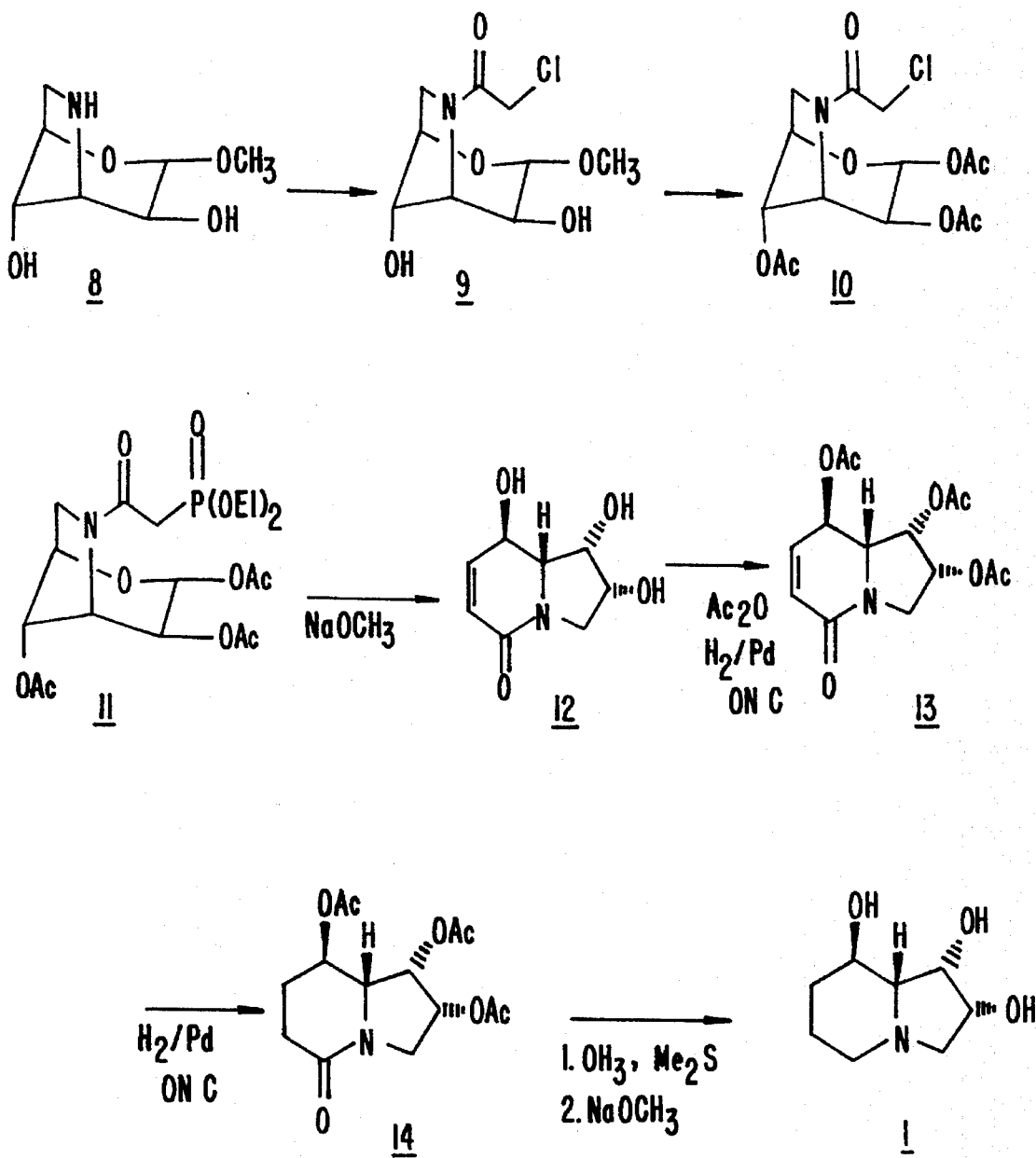
FIG. 7 is a general scheme for the synthesis of swainsonine from methyl 3,6-dideoxyimino-alpha-D-mannopyranoside.

The internal cyclization could be effected with an appropriate base such as a alkali metal alkoxide, or hydroxide, or carbonate) in a solvent such as an appropriate alcohol, acetonitrile. This reaction could be effected in a temperature range of about −10°–100° C., but usually involved mild conditions. The scheme depicting these reactions is illustrated in FIG. 7.

EXAMPLE 7

Synthesis of Methyl 3,6-dideoxychloroacetamido-alpha-D-mannopyranoside, 9. A solution of 1.5 moles (262.5 g) of crude methyl 3,6-dideoxyimino-alpha-D-mannopyranoside, 8, in 5.5 L of ethanol, and 6.5 moles (550 g) sodium bicarbonate was cooled to 10° C. Then 2.87 moles (490 g) chloroacetic anhydride was added in portions over 5 min. The temperature rose to 18° C. Stirring was continued for 2 h. The reaction mixture was filtered and evaporated. It was then applied to a column of 2.5 Kg SiO$_2$ in ethyl acetate, and the product was eluted with ethyl acetate. The solvent was evaporated and the crystalline product was washed with ethyl acetate to afford 241 g (0.96 mole; 64%) methyl 3,6-dideoxychloroacetamido-alpha-D-mannopyranoside (m.p. 146°–148° C).

$^1$H NMR (500 Mhz, DMSO-D6 87.3° C.): 4.5(1H; d, J=13.2 Hz); 4.29 (2H; complex); 4.17 (IH; br); 4.08 (IH; br d, J=5.25 Hz); 3.94 (IH; dd, J=2.5, 5.5 Hz); 3.84 (IH; br d; J=5.45 Hz); 3.46 (2H; s); 3.37 (3H; s).

EXAMPLE 8

Synthesis of 1,2,4-Tri-O-acetyl-3-6-dideoxychloroacetamido-alpha-D-mannopyranoside, 10. A mixture of 25.2 g (0.1 mole) methyl 3,6-dideoxychloroacetamido-alpha-D-mannopyranoside, 9, and 150 mL acetic anhydride were cooled to 10° C., and 4 mL sulfuric acid was added dropwise over 10 min. After 2 h the solution was allowed to warm to room temperature and stir overnight. Enough sodium acetate was added to quench the sulfuric acid, and the solvent was removed by vacuum distillation. Then, 500 mL water was added to the residue and the mixture stirred for 1 h. The thick oil that precipitated was extracted with dichloromethane. Evaporation afforded a light yellow oil that was evaporated with 3×100 mL toluene to yield oily crystals. These were washed with methanol to afford 10, 16.1 g, white crystalline solid (0.044 mole; 44%), of m.p. 147°–149° C.

$^1$H NMR (500 Mhz, CDCl3): 5.48–5.38 (3H; complex); 4.60 (1H; complex); 4.04–3.98 (2H; complex); 3.95 (2H; s); 3.74 (1H; brd; J=9.75 Hz); 2.15 (3H;s); 2.12 (3H; s); 2.04 (3H; s).

EXAMPLE 9

Synthesis of 1,2,4-tri-O-acetyl-3,6-dideoxydiethylphosphonoacetamidomannose, 11. A mixture of 5 g (0.0137 mole)1,2,4-tri-O-acetyl-3,6-dideoxychloroacetamido-alpha-D-mannopyranoside, 10, and 25 mL (0.146 mole) triethylphosphite was heated at 120° C. under argon for 13 h. The reaction mixture was stored in the freezer and crystalline product separated. The off-white crystals were filtered, washed with hexane and then dried to afford 5.12 g (0.011 mole; 80%) of 1,2,4-tri-O-acetyl-3,6-dideoxydiethylphosponoacetamidomannose of m.p. 80°–80.5° C.

The $^1$H NMR spectrum of 1,2,4-tri-O-acetyl-3,6-dideoxy-diethylphosponoacetamidomannose appeared as an approximately 3: 1 mixture. The presence of the minor component may be attributed to restricted rotation around the amide C-N bond. Chemical shift assignments were determined from a COSY 2-D spectrum of the sample after heating. The methylene protons adjacent to the phosphorous could not be definately observed from the COSY data and their assignment remains tentative.

The $^{13}$C spectrum was consistent with the proposed structure and the carbon resonances were differentiated in a DEPT spectrum. The chemical shift assignments are tentative since the $^{13}$C spectrum was complicated by the presence of extra signals particularly in the 68–70 ppm region.

| $^1$H Chemical Shifts in CDCl$_3$ | |
|---|---|
| Proton | Chemical Shift (ppm) |
| 1 | 5.877 |
| 2 | 5.717 |
| 3 | 4.675 |
| 4 | 5.427 |
| 5 | 5.323 |
| 6',6" | 4.187, 3.569 |
| CH$_2$P | 2.93a |
| OCH$_2$CH$_3$ | 4.15b |
| OCH$_2$CH$_3$ | 1.326, 1.313 |

| $^1$H—$^1$H Coupling Constants in CDCl$_3$ | |
|---|---|
| Protons | Coupling Constant (Hz) |
| | 2J |
| 6',6" | −11.3 |

| | 3J |
|---|---|
| 1,2 | 6.3 |
| 2,3 | 6.6 |
| 3,4 | 6.6 |
| 4,5 | 5.3 |
| 5,6' | 6.7 |
| 5,6" | 5.4 |

| $^{13}$C Chemical Shifts in CDCl$_3$a | |
|---|---|
| Carbon | Chemical Shift (ppm) |
| 1 | 96.0 |
| 2 | 70.3 |
| 3 | 56.1 |
| 4 | 69.7 |
| 5 | 56.9 |
| 6 | 50.3 |
| CH$_2$P | 34.6 (2JCP = 130.0 Hz) |
| OCH$_2$CH$_3$ | 62.8 |
| OCH$_2$CH$_3$ | 16.3 | a Tentative assignment only
b Overlapping multiplets

EXAMPLE 10

Synthesis of (1S,2R,8R,8aR)-1,2,8-trihydroxy-1,2,3,5,8,8a-hexahydro-5-oxyindolizine, 12. 1,2,4-tri-O-acetyl-3,6-dideoxydiethylphosponoacetamidomannose, 11, 750 mg (0.001609 mole) and 50 mg sodium in 20 mL methanol was stirred under argon for 1.5 h an −5°–0° C. Then 2 g silica gel was added. The solvent was evaporated and the residue was taken up in chloroform and chromatographed on SiO$_2$ in chloroform. Elution with chloroform-methanol 8: 2 afforded (1S,2R,8R,8aR)-1,2,8-trihydroxy-1,2,3,5,8,8a-hexahydro-5-oxyindolizine, 0.260 g (0.001404 mole; 87%) as a white crystalline solid of m.p. 180°–183° C.

$^1$H NMR (500 Mhz, CDCl3–CD3OD δ): 6.40 (1H; dd, J=1.5, 10 Hz); 5.62(1H; dd, J=2.5, 10.1 Hz); 4.69 (1H; dr; J=2, 11.9 Hz); 4.18–4.13 (1H; m); 4.08 (1H; t, J=3.5 Hz); 3.69 (1H; dd, J=8.2, 16.35 Hz); (3.52 (1H; d; J=3.1 Hz); 3.50 (1H; d, J=3.1 Hz); 3.10 (1H; dd, J=8.7, 11.6)

EXAMPLE 11

Synthesis of (1S,2R,8R,8aR)-1,2,8-triacetoxy-1,2,3,5,8,8a-hexahydro-5-oxyindoilzine, (1S,2R,8R,8aR)-1,2,8-trihydroxy-1,2,3,5,8,8a-hexahydro-5-oxyindolizine, 12, 0.250 g (0.00135 mole) and 3 mL pyridine were cooled in an ice-bath, and 1.5 mL acetic anhydride added. The mixture was allowed to warm to room temperature and stirred overnight. Cold water was added, and the mixture was stirred for 0.5 h. It was then extracted with dichloromethane. The combined organic extracts were washed with dilute hydrochloric acid, then sodium bicarbonate (aq.); dried and concentrated to afford (1S,2R,8R,8aR)-1,2,8-triacetoxy-1,2,3,5,8,8a-hexahydro-5-oxyindolizine, 13, as a pale green oil 0.5 g. This material could be crystallized from ether hexane to afford white crystalline solid of m.p. 108°–110° C.

$^1$H NMR (500 Mhz, CDCl3δ): 6.35 (1H; dd, J=1.6, 10.1 Hz); 5.92 (1H; dd, J=2.5, 10.1 Hz); 5.78 (1H; dr, J=1.8, 11.7 Hz); 5.53 (1H; t, J=3.6 Hz); 5.28 (1H; dr; 3.9,8.8 Hz); 4.03–3.98 (2H; complex); 3.45 (1H; dd, J=9.2, 11.6 Hz).

EXAMPLE 12

Synthesis of (1S,2R,8R,8aR)-1,2,8-triacetoxy-octahydro-5 oxyindolizine. 14. (1S,2R,8R,8aR)-1,2,8-triacetoxy-1,2,3,5,8,8a-hexahydro-5-oxyindolizine, 13, 22 g (0.070 mole), was hydrogenated at atmospheric pressure of hydrogen in 400 mL ethanol containing 3 g 10% Pd on carbon. The reaction was allowed to proceed overnight. The catalyst was filtered, and the filtrate was evaporated to dryness. The crystalline residue was taken up in ether and hexane and filtered to afford (1S,2R,8R,8aR)-1,2,8-triacetoxy-octahydro-5-oxyindolizine, 14, 21.4 g (0.068 mole; 97%) as a white crystalline solid of m.p. 146°–147° C. (lit. 143–145 ; A. C. Richardson et. al., Carb. Res., 136: 225(1985)).

$^1$H NMR (500 Mhz, CDCl3δ): 5.51 (1H; dd, J=1, 3.3 Hz), 5.29 (1H; ddd, J=3.9, 7.8); 5.02 (1H; ddd, J=4.25, 9.11, Hz); 3.83 (1H; dd, J=8.7, 12 Hz); 3.75 (1H; dd, J=2.6, 8.9 Hz); 3.52 (1H; dd, J=9.1, 11.8 Hz); 2.5 (1H; complex); 2.15 (1B; complex); 1.86 (1H; complex).

EXAMPLE 13

Figure 8:
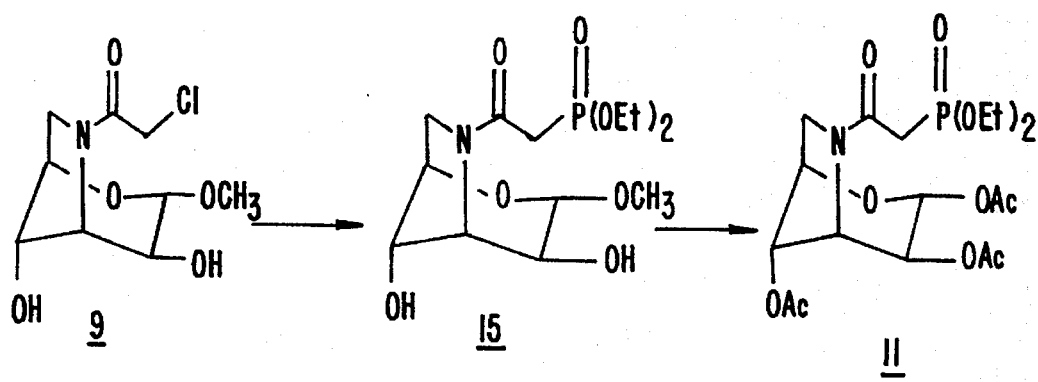
FIG. 8 is a general scheme for the preparation of the phosphonate intermediates for the production of swainsonine and its analogs.

Summary of the preparation of Swainsonine from Methyl 2,4-di-O-acetyl-3,6-dideoxyphosphonoacetamido-alpha-D-mannopyranoside. The preparation of the phosphonate could preceed the cleavage of the anomeric group, as shown in FIG. 8.

EXAMPLE 14

Synthesis of (1S,2R,8R,8aR)-1,2,8.triacetoxy-octahydro-5-oxyindolizine 14, from Methyl 2,4-di-O-acetyl-3,6-dideoxyphosphonoacetamido-alpha-D-mannopyranoside, 9. Methyl 2,4-di-O-acetyl-3,6-dideoxychloroacetamido-alpha-D-mannopyranoside, 8, 5 g (0.02 mole) and 20 mL triethylphoside were heated at 110° C. for 15 h. The solvent was removed at high vacuum and the residual oil stirred with 50 mL hexane and stored in the freezer for 2 h. The hexane was decanted to afford methyl 3,6-dideoxyphosphonoacetamido-alpha-D-mannopyranoside, 15, as a thick white oil. TLC analysis (SiO$_2$/CH$_2$Cl$_{12}$-MeOH) indicated that the compound was a single spot with Rf of 0.7 staining with 12 . This compound was evaporated from MeOH, and dried at high vacuum.

The residue was dissolved in acetic anhydride (30 mL) and cooled to −10° C. Then 0.8 mL sulfuric acid was added. The solution was allowed to warm to room temperature and stirred overnight under argon. Enough sodium acetate was added to quench the sulfuric acid, and the solvent was removed by vacuum distillation. The product was taken up in dichloromethane and washed with water, then sodium bicarbonate (aq.); dried, and concentrated to afford 4.65 g 1,2,4-tri-O-acetyl-3,6-dideoxydiethylphosphonoacetamido-D-mannose, 11, as a light yellow oil, which was converted, as described above to (1S,2R,8R,8aR)-1,2,8-triacetoxyoxyoctahydro-5-oxyindolizine, 0.8 g.

EXAMPLE 15

Figure 9:
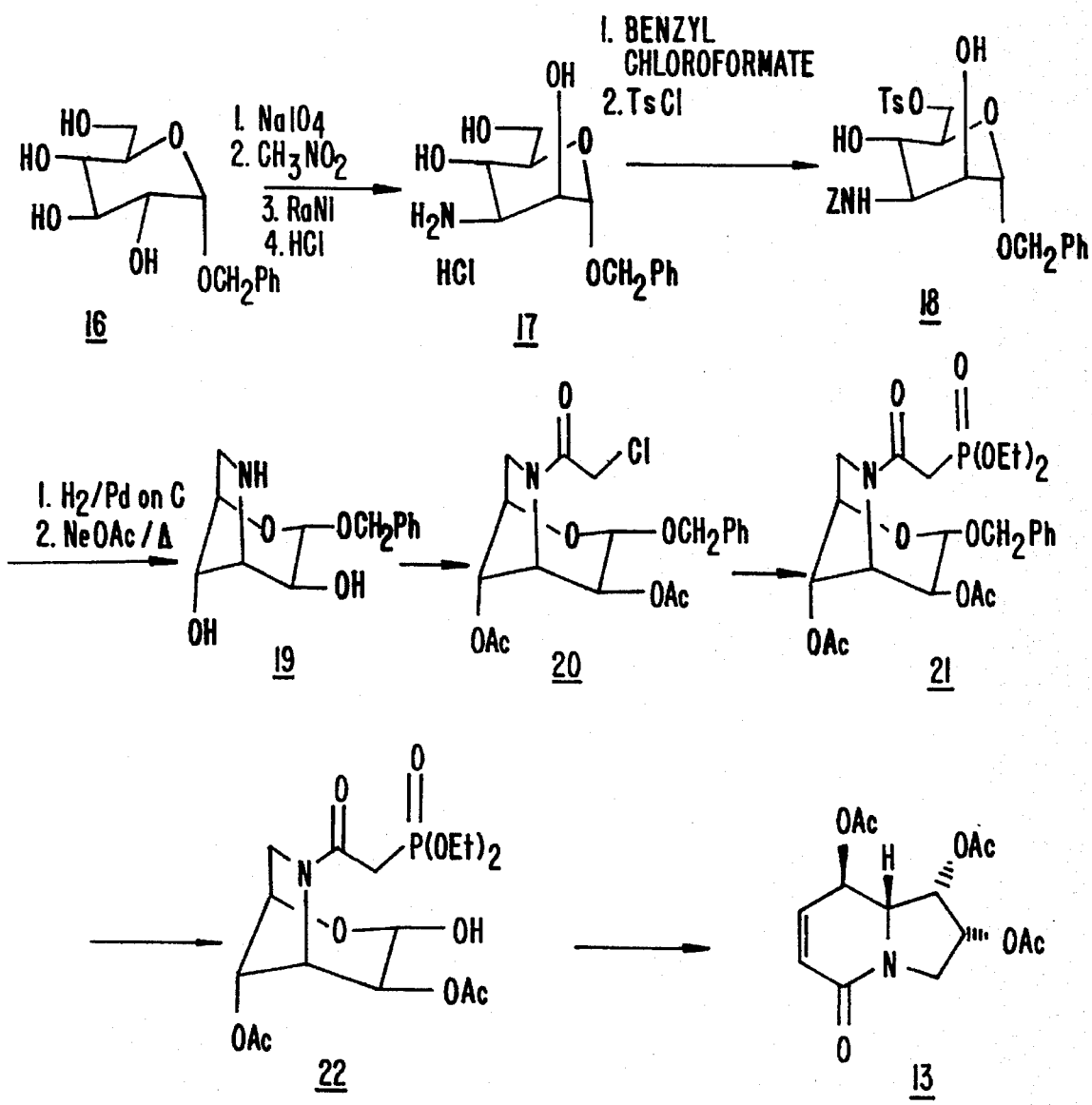
FIG. 9 is a general scheme for the synthesis of a precursor of swainsonine and its analogs from benzyl-alpha-O-glucopyranoside.

Summary of the synthesis of Swainsonine from Benzyl-Alpha-D-glucopyranoside. Benzyl-alpha-D-glucopyranoside, 16 (prepared from D-glucose using an adaptation of a method for the production of benzyl-alpha-D-mannopyranoside, G. W. J. Fleet et. al., Tetrahedron, 43: 3083 (1987)), was converted to benzyl 3,6-dideoxyimino-alpha-D-mannopyranoside, 19, via a series of reactions analogous to those described by A. C. Richardson et. al. [Carb. Res. 136: 225 (1985)]. Reaction with chloroacetic anhydride, followed by Arbuzov reaction with triethylphosphite gave the phosphonoacetamido derivative, 21. Hydrogenolysis of the anomeric protecting group and intramolecular Wittig reaction yielded (1S,2R,8R,8aR)-1,2,8-trihydroxy-1,2,3,5,8,8a-hexahydro-5-oxyindolizine, 13, the conversion of which to swainsonine has been previously demonstrated. The scheme illustrating these reactions is illustrated in FIG. 9.

EXAMPLE 16

Benzyl-alpha-D-glucopyranoside, 16. Acetyl chloride, 80 mL, was added carefully to 1.75 L benzyl alcohol. This was followed by the addition of 180 g glucose. The mixture was heated, with stirring, at 80° C. overnight; then cooled, and poured into a plastic bucket. The product was precipitated as an oil by the addition of ether (3 L) and hexane (15 L). The supernatant liquid was decanted, and the residual oil washed with ether-hexane 1:1 (10 L), then ether. This afforded benzyl-alpha-D-glucopyranoside as a semisolid which was filtered, crushed, and washed with ether, then hexane to afford 237.3 g (0.88 mole; 88%) white solid.

EXAMPLE 17

Benzyl 3-amino-3-deoxymannopyranoside, 17. In a 500 mL flask equipped with magnetic stirrer was placed 24 g benzyl glucose in 100 mL water. To this was added, in portions with cooling, 44 g sodium periodate. The temperature of the reaction mixture was kept below 20° C. After the addition of the periodate, the mixture was stirred for an additional 1 h. It was then neutralized with 8 g sodium bicarbonate, and 250 mL ethanol was added. The minute was then filtered and the filtrate was concentrated at a temperature below 40° C. The residue was taken up in 350 mL ethanol and filtered. The filtrate was treated with nitromethane (12 mL) followed by a solution of 2.4 g of sodium in 120 mL methanol. The reaction mixture was stirred at room temperature for 25 min., neutralized with Dowex H+ (about 150 mL), and filtered. The filtrate was concentrated and the residual syrup taken up in ethyl acetate and evaporated. It was then hydrogenated in ethanol (300 mL) with Rainey Nickel (about 0.5 teaspoon), at 180-80 p.s.i. pressure overnight. The catalyst was filtered, and the filtrate was treated with concentrated hydrochloric acid to bring the pH to about 7. The solution was then concentrated to dryness, and taken up in boiling ethanol (200 mL). Upon cooling in the freezer, methyl 3-amino-3-deoxy-alpha-D-mannopyranoside hydrochloride separated. This was filtered, and washed with ethanol to yield 17, 3.7 g white crystals. The proton NMR spectrum was complex.

EXAMPLE 18

Benzyl 3-carbobenzoxylamino-3-deoxymannopyranoside. Benzyl chloroformate (13.5 mL) was added dropwise to a suspension of benzyl 3-amino-3-deoxy-alpha-D-mannopyranoside hydrochloride (13.5 g; 0.0443 moles) and 15 g sodium bicarbonate in 50/50 ethanol water (100 mL). The reaction mixture was stirred at room temperature for 3 h and evaporated. The residue was taken up in ethanol and filtered. The filtrate was concentrated, and the residue was taken up in dichloromethane and filtered. The filtrate was concentrated and applied to a column of SiO$_2$. The column was washed with dichloromethane. Benzyl 3-carbobenzoxylamino-3-deoxymannopyranoside 14.1 g (0.035 mole), was then eluted with ethyl acetate.

EXAMPLE 19

Benzyl 3-carbobenzoxylamino-3-deoxy-6-O-para-toluenesulfonyl-alpha-D-mannopyranoside, 18. Benzyl 3-carbobenzoxylamino-3-deoxymannopyranoside 4.8 g (0.012 mole) was taken up in pyridine (35 mL) and 2.5 g p-toluenesulfonylchloride (0.0131 mole; 1.15 equivalent) was added. The solution was stirred at room temperature overnight. The solvent was removed at high vacuum, and the residue was taken up in dichloromethane and washed with water, dilute hydrochloric acid, and then sodium bicarbonate (aq.). The organic layer was dried by gravity filtration, concentrated and chromatographed on a column of SiO$_2$ made up in dichloromethane. Benzyl 3-carbobenzoxylamino-3-deoxy-6-O-para-tolueneslfonyl-alpha-D-mannopyranoside, 18, 4.6 g (0.0082 mole; 69%) was eluted with dichloromethane-ethyl acetate, 50:50 as an oil.

$^1$H NMR (500 Mhz, CDCl3δ): 7.77(2H; d, J=8.2 Hz); 7.32–7.24 (7H; complex); 5.66 (1H; brd; J=8.2 Hz); 5.08 (2H; dd; J=2.1, 18.4 Hz); 4.78(1H; s); 4.63(1H; d, J=11.9 Hz); 4.44 (1H; d, J=11.9 Hz); 4.30–4.25 (2H; complex); 3.95 (1H; m); 3.79–3.77 (2H; complex); 3.63 (1H; t, J=10 Hz); 2.40 (3H; s).

EXAMPLE 20

Benzyl 3,6-dideoxyimino-alpha-D-mannopyranoside, 19. Benzyl 3-carbobenzoxylamino-3-deoxy-6-O-para-tolueneslfonyl-alpha-D-mannopyranoside, 18, 2.6 g (0.00466 moles) was hydrogenated at atmospheric pressure of hydrogen overnight in 35 mL ethanol with 50 mg 10% Pd. The reaction mixture was filtered and 2.6 g sodium acetate was added. It was then heated at reflux under argon for 6.5 h. The reaction mixture was filtered and 8 g silica added to the filtrate. It was then evaporated to dryness and the residue applied to a column of SiO$_2$ made up in dichloromethane. Elution with dichloromethane-methanol 9: 1.5 afforded benzyl 3,6-dideoxyimino-alpha-D-mannopyranoside, 19, as a brown oil(1g; 85%) after evaporation.

$^1$H NMR (500 Mhz, CDCl3δ): 7.55–7.20 (5H; complex); 4.79 (2H; d, J=11.5 Hz); 4.71 (1H; d, J=7.2 Hz); 4.35 (1H; t, J=3.2 Hz); 4.18 (1H; dd, J=2.9, 5.5 Hz); 4.00 (1H; dd, J=2.7, 7.2 Hz); 3.87 (1H; dd, J=2.7, 5.5 Hz); 3.55 (1H; J=14.1 Hz); 3.46 (1H; dd, J=3.9, 14.1 Hz).

EXAMPLE 21

Benzyl 2,4-di-O-acetyl-3 ,6-dideoxychloroacetamido-alpha-D-mannopyranoside, 20. Chloroacetic anhydride, 1.02 g (0.00597 mole; 1.5 eq.) was added to a mixture of benzyl 3,6-dideoxyimino-alpha-D-mannopyranoside, 1 g (0.003984 mole), sodium bicarbonate 1.10 g (0.0131 mole; 3.3 eq) and 25 mL methanol cooled in an ice-water bath. The mixture was allowed to stir and come to room temperature over 2.5 h. It was then evaporated to dryness, and the residue was taken up in dichloromethane (50 mL) filtered, and evaporated to yield a residue of 1.2 g. This was treated with 15 mL acetic anhydride and 1.2 g sodium acetate and stirred at room temperature overnight. The reaction mixture was poured into water and stirred for 1 h. It was then extracted with dichloromethane. The combined organic extracts were washed with water, dried by filtration and concentrated. The residue was purified by chromatography on SiO$_2$ in dichloromethane-ethyl acetate 1:1 to afford benzyl 2,4-di-O-acetyl-3,6-dideoxychloroacetamido-alpha-D-mannopyranoside 20, 0.75 g (0.0018 mole; 46%) as a white crystalline solid, after crystallization from ethanol.

The spectra for these compounds were complicated due to rotational isomerism about the amid bond. Even at temperatures of about 90° C. in DMSO, free rotation was not seen. The spectra were, however, consistent with the proposed structures. The final proof for this sequence of reactions is the ultimate conversion of these intermediates to (1S,2R, 8R,8aR)-1,2,8-acetoxy-1,2,3,5,8,8a-hexahydro-5-oxyindolizine, 6.

EXAMPLE 22

Benzyl 2,4-all-O-acetyl-3,6-dideoxydiethylphosphonoacetamido-alpha-D-mannopyranoside, 21. Benzyl 2,4-all-O-acetyl-3,6-dideoxychloroacetamido-alpha-D-mannopyranoside, 20, 0.65 g (0.00157 mole) and triethyl phosphite (5 mL) were heated at 110–120° C. for 4.5 h with stirring under argon. The solvent was distilled at high vacuum, 50 mg of the residue was saved, and the rest carried on.

EXAMPLE 23

2,4-Di-O-acetyl-3,6-dideoxydiethylphosphonoacetamido-D-mannopyranose, 22. Crude benzyl 2,4-di-O-acetyl-3,6-dideoxydiethylphosphonoacetamido-alpha-D-mannopyranoside, 21, ethanol (10 mL), 2 88% formic acid and 0.1 g Pd black were heated at reflux overnight under argon with stirring. The reaction mixture was filtered and evaporated to dryness, and the residue was chromatographed on SiO$_2$ (40 g; dichloromethane-methanol 95: 5) to afford 0.57 g 2,4-di-O-acetyl-3,6-dideoxydiethylphosphonoacetamido-D-mannopyranose, as a yellow oil.

$^1$H NMR (500 Mhz, DMSO-D6 87.4° C.): 6.63(1H; d, J=735 Hz); 5.01 (1H; t J=7.1 Hz); 4.78 (1H; br d); 4.70(1H; dd); 4.61 (1H; brd; J=7Hz); 4.50 (1H; brs); 4.10–3.97 (5H; Complex); 3.84 (1H; dd; J=3.9, 11.8 Hz); 2.13 (3H; s); 1.92 (1H;s).

EXAMPLE 24

Conversion of 2,4,-Di-O-acetyl-3,6-dideoxydiethylphosphonoacetamido-D-mannopyranose, 22, to (1S,2R, 8R,8aR)-1,2,8-triacetoxy-1 ,2,3,5,8,8a-hexahydro-5-oxyindolizine, 13. 2,4-di-O-acetyl-3,6-dideoxydiethylphosphonoacetamido-D-mannopyranose 0.040 g, 50 mg dry potassium carbonate and 5 mL ethanol were stirred under argon at room temperature overnight. TLC analysis (SiO$_2$/dichloromethane-methanol 4:1) indicated complete conversion to (1S,2R,8R,8aR)-1,2,8-trihydroxy-1,2,3,5,8,8a-hexahydro-5-oxyindolizine (confirmed by comparison with an authentic sample, and subsequent conversion to (1S,2R,8R,8aR)-1,2,8-acetoxy-1 ,2,3,5,8,8a-hexahydro-5-oxyindolizine). The reaction mixture was filtered, and evaporated. The residue was acetylated with acetic anhydride (2 mL) and a catalytic amount of dimethylaminopyridine (10 mg). The reaction mixture was poured into dilute hydrochloric acid, and extracted with dichloromethane. The combined organic extracts were washed with sodium bicarbonate (aq.) dried and concentrated to afford (1S,2R,8R,8aR)-1,2,8-acetoxy-1,2,3,5,8,8a-hexahydro-5-oxyindolizine as a green oil with TLC identical to that of authentic material.

Compounds derived from (1S,2R,8R,8aR)-1,2,8-triacetoxy-1,2,3,5,8,8a-hexahydro-5-oxyindolizine.

The enamide function of (1S,2R,8R,8aR)-1,2,8-triacetoxy-1,2,3,5,8,8a-hexahydro-5-oxyindolizine may be subjected to various standard chemical reactions to afford derivatives which may be converted to substituted swainsonine.

1. By addition of a nucleophilic reagent in a 1,4-manner to the enamide function, and subsequent conversion to a substituted swainsonine analogue.

Figure 10:
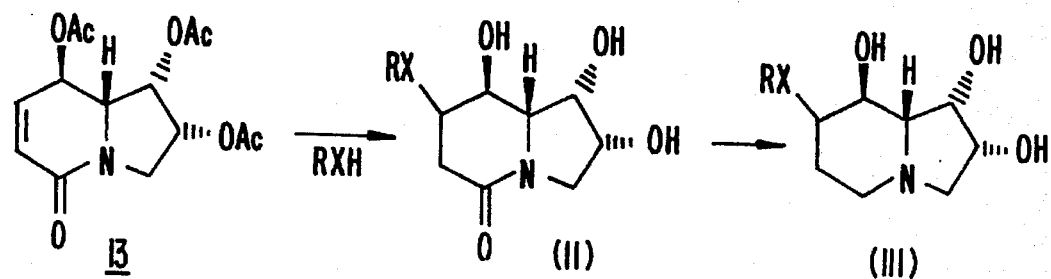
FIG. 10 is a general scheme for the systhesis of compounds derived from (1S,2S,8R,8aR)-1,2,8-triacetoxy-1,2, 3,5,8,8a-hexahydro-5-oxyindolizine by the addition of a nucleophilic reagent in an 1,4 manner to the enamide function.

The scheme depicting these reactions is illustrated in FIG. 10, where RX is selected from the group consisting of MeOH, EtOH, PrOH, i-PrOH, BuOH, pentanol, hexanol, octanol, decanol, dodecanol, $NH_3$, methylamine, dimethylamine, ethylamine, diethylamine, propylamine, dipropylamine, isopropylamine, butylamine, dibutylamine, hexylamine, dihexylamine, dodecylamine, aniline, p-nitroaniline, sodium sulfide, ethanethiol, propanethiol, butanethiol, pentanethiol, hexanethiol, thiophenol, p-mercaptobenzoic acid, p-nitrothiophenol, and the salts of these compounds, potassium chloride, potassium fluoride, potassium iodide, sodium chloride, sodium fluoride, sodium iodide, sodium azide, potassium cyanide, sodium cyanide, sodiumdiethylmalonate, methylmagnesium bromide, phenylmagnesium bromide, allylmagnesium bromide, methyllithium, butyllithium, phenyllithium, lithium, and dimethylcuprate.

Examples of this reaction include the addition of alcohols, amines, sulfhydryl groups and organometallics (which by varying the reaction conditions, may also add in 1.2 fashion to the enamide to afford useful products). This addition may be catalyzed by a base.

EXAMPLE 25

Synthesis of 7-ethoxy-(1S,2R,8R,8aR)-1,2,8-triacetoxy-octahydro-5-oxyindolizine. 24. (1S,2R,8R,8aR)-1,2,8-trihydroxy-1,2,3,5,8,8a-hexahydro-5-oxyindolizine, 13, 0.85 g (0.00457 mole), and 0.5 g potassium carbonate were heated at reflux for 24 h under argon in 50 mL ethanol. The mixture was then filtered through silica gel, and the filter-cake was washed with methanol. The filtrate was concentrated to afford crude 7-ethoxy-(1S,2R,8R,8aR)-1,2,8-hydroxy-octahydro-5-oxyindolizine 23, as a brown foam. This was taken up in 20 mL pyridine and 10 mL acetic anhydride and allowed to stir at room temperature overnight. The reaction mixture was poured into water and extracted with dichloromethane. The combined organic extracts were washed sequentially with water, dilute hydrochloric acid, water, sodium bicarbonate (aq.), then dried, and concentrated. The residual oil was purified by chromatography ($SiO_2$; hexane-ethylacetate) to afford 7-ethoxy-(1S,2R,8R,8aR)-1,2,8-triacetoxy-octahydro-5-oxyindolizine 24, as white crystalline solid, 0.71 g. Proton NMR showed a mixture of ethoxy isomers.

EXAMPLE 26

Synthesis of 7-ethoxy-(1S,2R,8R,8aR)-1,2,8-trihydroxy-octahydroindolizine (7-ethoxyswainsonine) 25. To 7-ethoxy-(1S,2R,8R,8aR)-1,2,8-triacetoxy-octahydro-5-oxyindolizine, 24, 0.65 g (0.0018 mole), in 25 mL tetrahydrofuran (THF) was added 4 mL of a 2M solution of borane-dimethylsulfide in THF. The solution was stirred at room temperature under argon overnight. Methanol was then added carefully to quench the excess borane, and the solution concentrated to dryness. The residue was evaporated from methanol (2×50 mL). Then a solution of 0.1 g sodium in 50 mL methanol was added. The reaction mixture was stirred at room temperature for 6 h and was evaporated to dryness. The residue was taken up in 15 mL of 50% trifluoroacetic acid. After being stirred for 10 min., the solvent was removed at high vacuum, and the residue was evaporated from methanol. The product was applied to a column of Dowex H+ in methanol. The column was washed with methanol, and the product eluded with concentrated ammonium hydroxide. The fractions containing the desired product were combined and concentrated. The residue (0.4 g) was chromatographed ($SiO_2$; chloroformmethanol) to afford 7-ethoxyswainsonine, 25, 0.09 g (0.000415 mole; 23%) as a crystalline solid. Proton NMR showed a mixture of ethoxy isomers.

2. By the addition of a reagent to the double bond.

Figure 11:
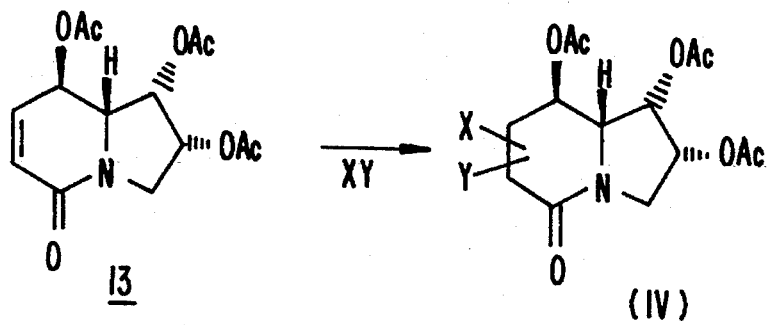
FIG. 11 is a general scheme for the synthesis of compounds derived from (1S,2R,8R,8aR)-1,2,8, -triacetoxy-1,2, 3,5,8,8a, -hexahydro-5-oxyindolizine by the addition of a reagent to the double bond.

The scheme for this reaction is depicted in FIG. 11, where XY is selected from the group consisting of BrOH, $Br_2$/AgOAc, $Br_2$, $Cl_2$, $I_2$, BrCN, HBr, HCl, HF, HI, phenylselenium chloride, phenylselenium bromide, phenylselenium iodide, butadiene, and cyclopentadiene. This includes, but is not limited to such reactions as hydrohalogenation, hydrocyanation, hydroformylation, halogenation and cycloadditions [J. March, Advanced Organic Chemistry, 3rd Ed. J. Wiley & Son (1985), Ch 15].

Figure 12:
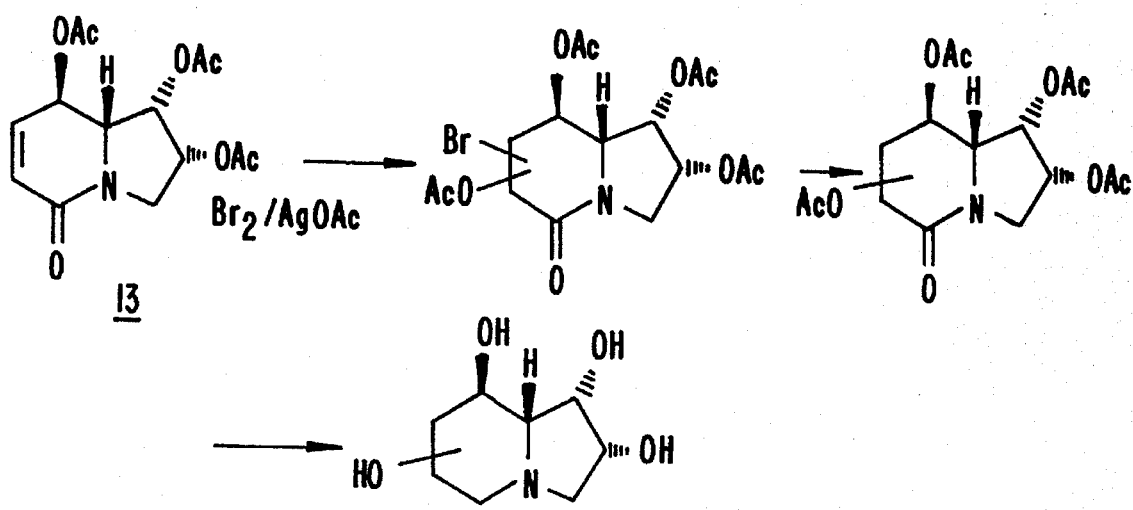
FIG. 12 is a general scheme leading to the synthesis of swainsonine analogs via bromoacetate intermediates.

An example of this is the addition of silver acetate and bromine to afford a mixture of bromoacetates. NMR analysis indicated that 13 affords a mixture of 2 bromoacetates. Such bromoacetates may be converted to epoxides (see P. Vogel et. al., J. Org. Chem., 56: 2128 (1991)). The bromine group can also be reduced with a suitable reducing agent and the product converted to a hydroxy substituted swainsonine. Examples of suitable reducing agents for bromides include tributyltinhydride [J. Org. Chem., 56: 99 (1991)]. The scheme depicting this reaction is illustrated in FIG. 12.

Figure 13:
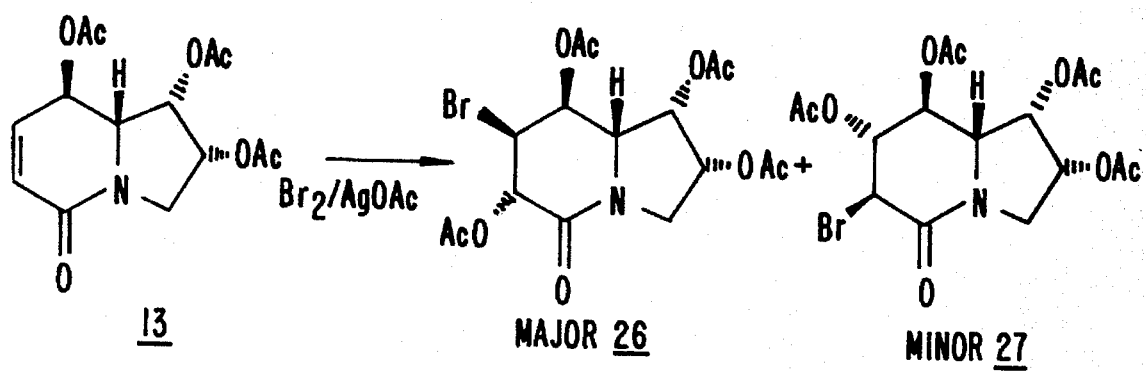
FIG. 13 is a general scheme for the synthesis of swainsonine analogs via bromide intermediates.

The reductive cleavage of the bromide mixture afforded as the major product 1S-1-alpha-2-alpha-6-alpha-8-β-tetra-O-acetyl-8a-β-octahydro-5-oxo-indolizine, 29. This structure was confimed by NMR spectral analysis (including assignments based upon a combination of the COSY 2-D and NOE difference experiments) of the swainsonine analogue 1S-1-alpha-2-alpha-6-alpha-8β-tetrahydroxy-8a-β-octahydroindolizine derived from it by reduction of the lactam, and subsequent deacetylation. This indicates that as expected the bromonium ion attacked at the sterically less hindered exo face of the molecule. Attack of the acetate from the endo face afforded the major product arising from addition at 6 position. It is postulated that the minor product is the 7-alpha-acetoxy-6-beta-bromoderivative. The scheme for these reactions is depicted in FIG. 13.

The reduction of 26 with $BH_3.Me_2S$ in the manner described for the synthesis of 7-ethoxyswainsonine, 25, afforded 1S-7-β-bromo-1-alpha-2-alpha-6-alpha-8β-tetrahydroxy-8a-β-octahydroindelizine, 28.

EXAMPLE 27

Addition of Bromo-acetate to (1S,2R,8R,8aR)-1,2,8-triacetoxy-1,2,3,5,8,8a-hexahydro-5-oxyindolizine. A suspension of (1S,2R,8R,8aR)-1,2,8-triacetoxy-1,2,3,5,8,8a-hexahydro-5-oxyindolizine, 3.11 g (0.01 mole), and 6g silver acetate in 30 mL acetic acid and 15 mL-acetic anhydride was cooled to about 5° C. and 4.8 g (0.03 mole) bromine in 28.5 mL acetic acid was added dropwise over 30 min. After 5 min. of stirring, under argon, no starting material remained, as determined by TLC analysis. The reaction mixture was poured into water (1 L), and ice, and stirred overnight. The mixture was extracted with dichloromethane. The combined organic extracts were washed with water, dried, and evaporated to dryness to afford a mixture of bromoacetates 26 and 27 as an off-white foam (3.65 g; 0.0081 mole; 81% yield). This product was carried on.

Proton NMR spectral analysis showed a mixture of bromoacetates.

EXAMPLE 28

Reduction of 6,7-Acetoxy, bromo-(1S,2R,8R,8aR)-1,2,8-triacetoxy-octahydro-5-oxyindolizine 26, 27. The product of the addition of bromine-silveracetate to (1S,2R,8R,8aR)-1,2,8-triacetoxy-1,2,3,5,8,8a-hexahydro-5-oxyindolizine, prepared as described above, [3.6 g (0.008 mole)] was dissolved in 100 mL dry toluene. The solution was heated to 100° C. under argon with stirring, and a solution of tributyltin hydride (2.32 g; 0.016 mole) and AIBN (120 mg) in 35 mL toluene was added dropwise over 40 min. The resulting solution was heated at reflux for 1 h, and a second portion of tributyltin hydride (2.32 g; 0.016 mole) and AIBN (120 mg) in 35 mL toluene was added. The reaction mixture was refluxed for a further 1 h. The solvent was evaporated, and the residual yellow oil was chromatographed ($SiO_2$; hexane-ethylacetate ). Two products were separated (Rf 0.62, 1.15 g mp. 134–136; Rf 0.57, 0.63 g m.p. 166–169). The structure of the high Rf product was determined to be 1S-5-oxo-1-alpha-2-alpha-6-alpha-8β-tetra-O-acetyl-8a-β-octahydroindolizine 29, by spectral analysis of the product of its subsequent reduction and deacetylation (vide infra). The structure of the low Rf product is inferred to be 1S-1-alpha-2-alpha-7-alpha-8β-tetra-O-acetyl-8a-β-octahydro-5-oxo-indolizine 30. NMR spectral analysis of the mixture showed the product ratio to be about 1.75: 1, with the high Rf product being the major or component.

EXAMPLE 29

Synthesis of 1S-1-alpha-2-alpha-6-alpha-8β-tetrahydroxy-8a-β-octahydroindolizine, 31. 1S-1-alpha-2-alpha-6-alpha-8β-tetra-O-acetyl-8a-β-octahydro-5-oxo-indolizine, 0.371 g (0.0001) was converted to 1S-1alpha-2-alpha-6-alpha-8β-tetrahydroxy-8a-β-octahydroindolizine, 0.18 g (0.000952 mole; 95% yield) as described above (see Synthesis of 7-ethoxy-(1S, 1R, 8R,8aR)-1,2,8-trihydroxy-octahydroindoilzine (7-ethoxyswainsonine)).

$^1$H NMR (500 Mhz, $D_2O_5δ$): 4.22 (1H; complex); 4.12 (1H; dd, J=3.9, 4 Hz); 3.98 (1H; complex); 2.84 (1H; d, J=12.4 Hz); 2.78(1H; dd, J=2.1, 10.8 Hz); 2.46(1H; dd, J=8.6, 8.6 Hz); 2.09 (1H; d, J=2.3 Hz); 2.05 (1H; d, J=13.5 Hz); 1.87 (1H; d, J=6 Hz), 1.35 (1H; ddd, J=3.2, 12.9 Hz).

Proton chemical shifts were assigned by a combination of the COSY 2-D and NOE difference experiments. By comparison with previous compounds in this series, the proton at C-2 was assigned to the lowest field multiplet at 4.222 ppm. In the COSY contour plot H-2 displayed a cross-peak to the multiplet at 4.124, 2.464 and 2.777 ppm. The latter pair of signals at 2.464 and 2.777 ppm were also coupled to each other. Based on these correlations the 4.12 4 ppm signal was assigned to H-1 while the other signals were attributed to the methylene protons on C-3. These methylene protons were differentiated by an NOE difference experiment in which saturation of H-2 enhanced the C-3 proton at 2.464 ppm (H-3a). Other protons enhance in the NOE experiment were H-1 and a weak enhancement of the ring junction proton H-8a. An energy minimized structure was generated which showed H-2 and H-3a in close proximity (2.33 A). This structure also produced vicinal coupling constants for these protons which agreed to within ±1.0 Hz of the observed values (see Table below).

Assignment of the six-membered ring protons was complicated by the overlap of the methine protons (3.99 ppm) on the hydoxylated carbons C-8 and C-6 or C-7. In the COSY spectrum the methine protons showed correlations to signals at 2.093, 2.848, 1.350, 2.049 ppm and a weak cross-peak to H-8a at 1,874 pm. The signals at 2.093 and 2,848 ppm were coupled to each other and 1.350 and 2.049 ppm were also coupled suggesting that these were the methylene protons of the six-membered ring. The critical observation was that there were no cross-peaks between these signals other than a weak cross-peak between 2.848 and 2.049 pm. The interpretation is that the hydroxyl group is located on C-6, and has alpha stereochemistry.

| $^1$H Chemical Shifts in $D_2O$ | |
|---|---|
| Proton | Chemical Shift (ppm) |
| H-1 | 4.124 |
| H-2 | 4.222 |
| H-3a | 2.464 |
| H-3b | 2.777 |
| H-5a | 2.093 |
| H-5b | 2.848 |
| H-6 | 3.99 |
| H-7a | 2.049 |
| H-8 | 3.99 |
| H-8a | 1.874 |

| $^1$H Coupling Constants In $D_2O$ | |
|---|---|
| Protons | Vicinal Coupling Constants (Hz) |
| 1-2 | 5.9 |
| 1-2a | 3.6 |
| 2-3a | 8.1 |
| 2-3b | 2.8 |
| 3a-3b | −10.8 |
| 5a-5b | −12.4 |
| 5a-6 | |
| 5b-6 | 2.1 |
| 6-7a | 4.7 |
| 6-7b | 3.3 |
| 7a-7b | −13.5 |
| 7a-8 | 11.6 |
| 7b-8 | 2.9 |
| 8-8a | 9.6 |

| Long-range Coupling Constants (Hz) | |
|---|---|
| 5b-7b (4J) | 2.0 |

Figure 14:
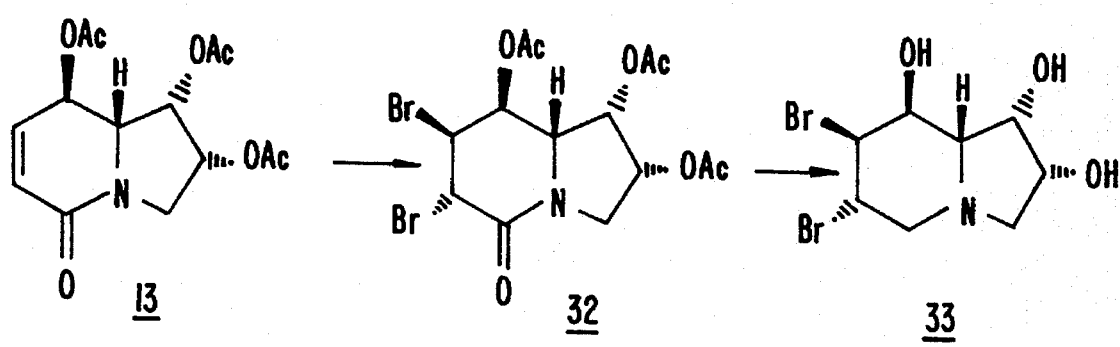
FIG. 14 is a general scheme for the synthesis of dibromoswainsonine.

Bromine adds to the double bond to afford predominantly the 6-alpha-7-beta-bromide. This compound was converted by reduction of the amide to the dibromoswainsonine. The scheme is depicted in FIG. 14.

EXAMPLE 30

Synthesis of 1S-6-alpha, 7β-dibromo-1-alpha-2-8β-tri-O-acetyl-8a-β-octahydro-5-oxyindolizine, 32. To a solution of 0.150 g (0.000482 mole) (1S,2R,8R,8aR)-1,2,8-trihydroxy-1,2,3,5,8a-hexahydro-5-oxyindolizine, 13, in 2 mL dichloromethane, cooled in an ice bath was added a solution of 26 uL of bromine in 1 mL dichloromethane. The reaction mixture was stirred for 2 h at 10°–15° C. and evaporated to dryness. The residue was purified by chromatography ($SiO_2$; ethyl acetate-hexane) to afford 1S-6-alpha, 7β-dibromo-1-alpha-2-alpha-8β-tri-O-acetyl 8a-β-octahydro-5-oxyindolizine as a white solid 0.157 g (0.0003339 mole; 70%) of m.p. 170°–177° C. after crystallization from ethylacetate-hexane.

EXAMPLE 31

Synthesis of 1S-6-alpha, 7β-dibromo-1-alpha-2-alpha-8β-trihydroxy-8a -β-octahydroindolizine, 33. 1S-6-alpha, 7β-dibromo-1-alpha-2-8β-tri-O-acetyl-8a-β-octahydro-5-oxyindolizine 0.150 g (0.000319 mole) was converted to 1S-6-alpha, 7β-dibromo-1-alpha-2-alpha-8β-trihydroxy-8a-β-octahydroindolizine, 0.095 g (0.000276 mole; 86% yield), as described above (see synthesis of 7-ethoxyswainsonine).

¹H NMR (500 Mhz, DMSO-d₆+1 Drop D₂O₆δ): 4.769 (1H; complex H-6); 4.739 (1H; complex; H-7); 4.138 (1H; dd, J=3.6, 9.2 Hz; H-8); 4.093 (1H; m, H-2); 3.935 (1H; dd, J=3.6, 6.03; H-1); 2.907 (1H; complex; H-5 alpha); 2.851 (1H; dd, J=2.2, 13.5 Hz; H-5β); 2.773 (1H; dd, J=2.5, 9.8 Hz; H-3 alpha); 2.441 (1H; dd, J=7.8, 9.8 Hz; H-3δ).

Proton chemical shifts were assigned by a combination of decoupling and NOE difference experiments. The stereochemistry at C-7 and C-6 was confirmed by the observation of an NOE between H-8 (4.138 ppm and H-7 (4.739 ppm).

3. By the oxidation of the double bond.

Figure 15:
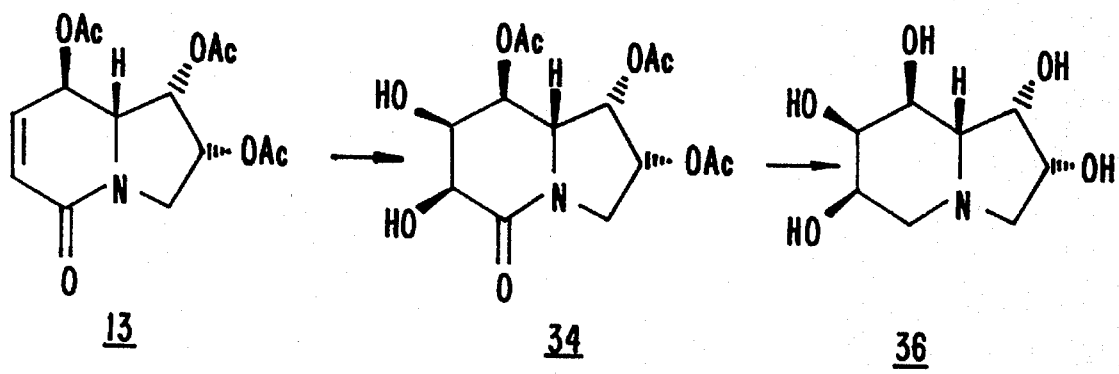
FIG. 15 is a general scheme for the synthesis of swainsonine analogs from (1S,2S,8R,8aR)-triacetoxy-1,2,3,5,8,8a-hexahydro-5-oxyindolizline by oxidation of the double bond.

Examples of this include osmium tetroxide oxidation (e.g. K. B. Sharpless et. al, J. Amer. Chem. Soc., 111: 1123 (1989)). The diol product of this reaction can be converted into the swainsonine diol by acetylation, followed by reduction of the amide, and subsequent deacetylation. The scheme depicting these reactions is illustrated in FIG. 15. Also included in this group of reactions is epoxidation [Tetrahedron, 39: 2323, 1983].

EXAMPLE 32

Synthesis of 1S-6β, 7β-dihydroxy-1-alpha-2-alpha-8β-tri-O-acetyl-8a-β-octahydro-5-oxyindolizine. 34. A solution of 0.176 g (0.0015 mole) N-methylmorpholine-N-oxide and 18 mg osmium tetroxide (0.00007 mole) in 10 mL acetonwater 10: 1, was cooled to 0° C. and 0.332 g (0.001 mole) (1S,2R,8R,8aR)-1,2,8-trihydroxy-1,2,3,5,8,8a-hexahydro-5-oxyindolizine, 13, was added. The reaction mixture was allowed to come to room temperature and stir overnight. Sodium metabisulphite, 2g, was added and the mixture stirred for 30 min. It was then diluted with dichloromethane, dried over sodium sulphate, filtered and concentrated. The residue was purified by chromatography (SiO₂; ethyl acetate) to afford a white solid 0.32 g, which was taken up in ether and filtered to yield 1S-6β, 7β-dihydroxy-1-alpha-2-alpha-8β-tri-O-acetyl-8a-β-octahydro-5-oxyindolizine, 34, 0.24g (0.0006557 mole; 66% yield).

¹H NMR (500 Mhz, CDCl3δ): 5.49(1H; dd, J=2.8, 4.1 Hz); 5.36(1H; ddd; J=4.1,8.5 Hz); 5.14 (1H; dd, J=1.5, 9.8 Hz); 4.40(1H; s); 4.21 (1H; dd, J=2.3, 9.8 Hz); 4.12(1H; d, J=2.1 Hz); 3.94 (1H; dd, J=9, 12.3 Hz); 3.43 (IH; dd, J=8.3, 12.3 Hz); 2.10(6H; s); 2.01 (3H; s).

The majority of the ¹H chemical shift assignments, below, follow from comparison with the compound containing the C6–C7 double bond ((1S,2R,8R,8aR)-1,2,8-triacetoxy-1,2,3,5,8,8a-hexahydro-5-oxyindolizine 13). The assignments of H-6 and H-7 are based on the NOE difference experiments. Both H-6 and H-7 displayed an enhancement of H-8 when they were saturated. These NOE results also indicate that the stereochemistry of oxidation was such that the protons on C-6 and C-7 are cis to that on C-8. In addition there was no large vicinal coupling constant observed between the C-7 and C-8 protons.

| ¹H Chemical Shifts In CDCl₃ | |
| --- | --- |
| Proton | Chemical shift (ppm) |
| 1 | 5.492 |
| 2 | 5.361 |
| 3a,b | 3.941, 3.431 |
| 6 | 4.406 |
| 7 | 4.120 |
| 8 | 5.142 |
| 8a | 4.222 |

| ¹H Coupling constants In CDCl3 | |
| --- | --- |
| Protons | Coupling Constant (Hz) |
| 3J | |
| 1,2 | 4.1 |
| 1,8a | 2.2 |
| 2,3a | 9.9 |
| 2,3b | 8.6 |
| 8,8a | 9.8 |
| 3j | |
| 3a,3b | –12.3 |

EXAMPLE 33

Synthesis of 1S-1-alpha-2-alpha-6β, 7β-8β-penta-O-acetyl-8a-β-octahydro-5-oxyindolizine. 35. To 1S-6β, 7β-dihydroxy-1-alpha-2-alpha-8, β-tri-O-acetyl-8a-β-octahydro-5-oxyindolizine, 0.20 g (0.000546 mole), was added 8 mL pyridine, 5 mL- acetic anhydride and 10 mg dimethylaminopyridine. The mixture was stirred at room temperature under argon overnight. It was then poured into dilute hydrochloric acid (1N; 150 mL), stirred for 15 min, and extracted with dichloromethane. The combined organic extracts were washed with dilute hydrochloric acid, then sodium bicarbonate (aq.), dried, and concentrated. The residue was purified by chromatography (SiO₂; methylenechloride-ethylacetate) to afford 1S-1-alpha-2-alpha-6β, 7β-8β-penta-O-acetyl-8a-β-octahydro-5-oxyindolizine as a yellow crystalline solid, 200 mg (0.000444 mole; 81% yield).

1H NMR (500 Mhz, CDCl3δ): 5.69 (1H; m; J=2.2 Hz); 5.55(1H; d, J=3.4 Hz); 5.48 (1H; d, J=3.1 Hz); 5.38 (1H; ddd, J=3.9, 8.6); 5.26(1H; dd, J=1.7, 9.8 Hz); 4.08(1H; dd, J=2.4, 12.1 Hz); 3.94(1H; dd, J=8.9, 12.3 Hz); 3.47(1H; dd, J=8.6, 12.3 Hz); 2.14 (3H; s); 2.12 (3H; s); 2.11 (3H; s); 2.03 (3H; s), 2.01 (3H; s).

EXAMPLE 34

Synthesis of 1S-1-alpha-2-alpha-6β, 7β-8β-pentahydroxy-8a-β-octahydroindolizine. 36. 1S-alpha-2-alpha-6β, 7β-8β-penta-O-acetyl-8a-β-octahydro-5-oxyindolizine 0.110 g (0.0002444 mole) was converted to 1S-1-alpha-2-alpha-6β, 7β-8β-pentahydroxy-8a-β-octahydroindolizine, 0. 045 g (0.000295 mole; 90% yield) as described above (see Synthesis of 7-ethoxy-(1S,2R,8R,8aR)-1,2,8-trihydroxyoctahydroindolizine (7-ethoxyswainsonine)).

1H NMR (500 Mhz, D2O δ): 4.28 (1H; complex); 4.07 (1H; dd, J=3.7, 5.7 Hz); 3.95(1H; m, J=2.8 Hz); 3.71 (1H; dd, J=2.8, 10.2 Hz); 3.67 (1H; ddd, J=2.8, 4.9,7.9 Hz); 2.75 (2H; complex); 2.54 (1H; br); 2.28 (1H; br); 2.15 (1H; br).

4. By reduction

Figure 16:
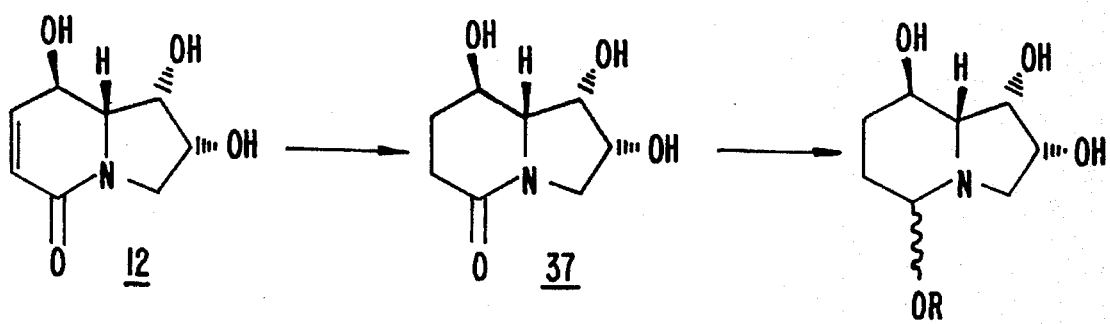
FIG. 16 is a general scheme for the synthesis of swainsonine analogs from (1S,2S,8R,8aR)-trihydroxy-1,2,3,5,8,8a-hexahydro-5-oxyindolizine by reduction.
Figure 17:
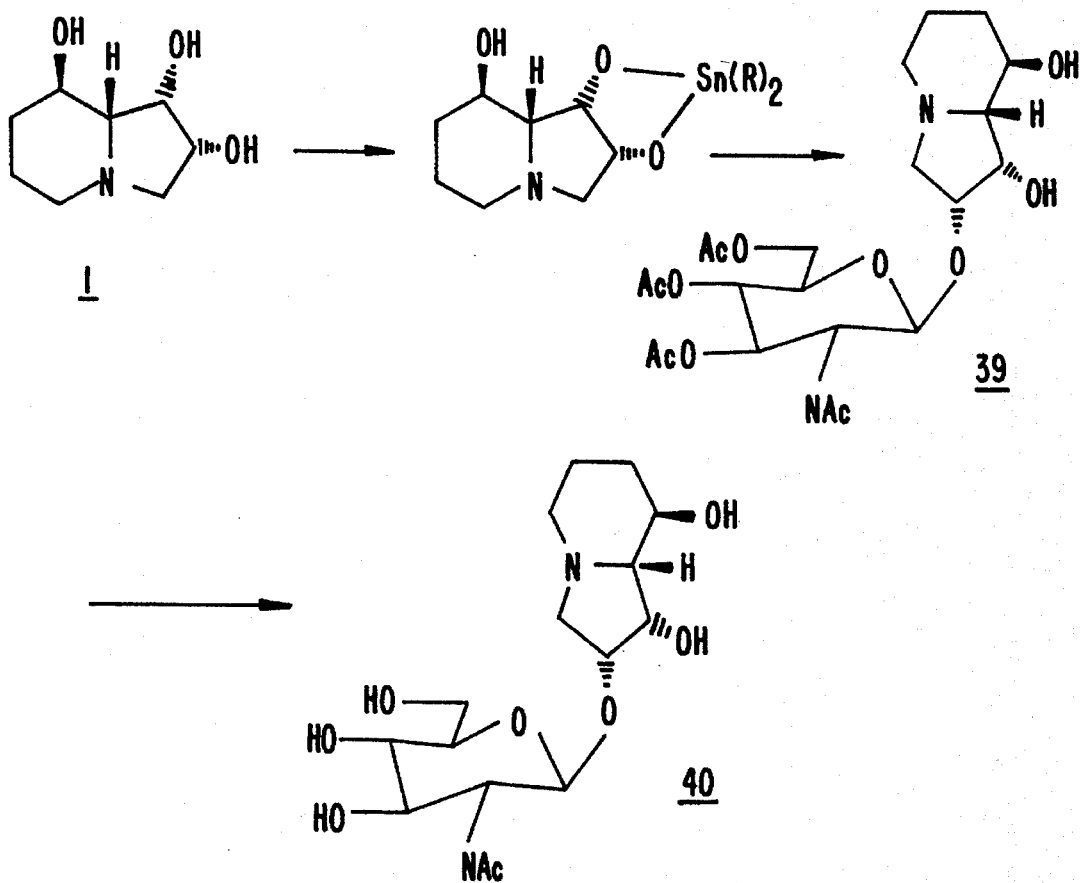
FIG. 17 is a general scheme for the synthesis of glycosides of swainsonine.

The amide, 1S-1-alpha-2-alpha-8β-trihydroxy-8a-β-octahydro-5-oxy-indolizine, produced by hydrogenation of (1S,2R,8R,8aR)-1,2,8-hydroxy-1,2,3,5,8,8a-hexahydro-5-oxyindolizine can be reduced with sodium borohydride, or other suitable reducing agents in an appropriate solvent to afford the aminoalcohol, or alkoxide. The scheme depicting these reactions is illustrated in FIG. 16.

EXAMPLE 35

Synthesis of 1S-5-oxy-1-alpha-2-alpha-8β-trihydroxy-8a-β-octahydroindolizine. 37. (1S,2R,8R,8aR)-1,2,8-hydroxy-1,2,3,5,8,8a-hexahydro-5-oxyindolizine, 12, 460 mg (0.00248 mole) was hydrogenated in methanol at atmospheric pressure of hydrogen, until hydrogen uptake ceased (1 h), employing 50 mg 10% Pd on carbon catalyst. Filtration of the catalyst, and concentration of the filtrate afforded 1S-1-alpha-2-alpha-8β-trihydroxy-8a-β-octahydro-5-oxyindolizine, 440 mg (0.00235 mole; 95% yield) as a white foam.

EXAMPLE 36

Synthesis of 1S-5-ethoxy-1-alpha-2-alpha-8β-trihydroxy-8a-β-octahydroindolizine, 38. To a solution of 1S-5-oxy-1-alpha-2-alpha-8β-trihydroxy-8a-β-octahydroindolizine, 440 mg (0.00235 mole) in 20 mL ethanol cooled to −10° C., was added sodium borohydride, 360 mg (0.0094 mole). Every 15 min., 1 drop of 2N HCl in ethanol was added. After 6 h. TLC analysis ($SiO_2$-chloroformmethanol 4:1) demonstrated the absence of starting material. The pH was adjusted to 2 with 2N HCl in ethanol, and the reaction mixture was stirred at below 0° C. for 1 h. Then about 2 g silica was added. The mixture was concentrated to dryness, and the residue purified by chromatography ($SiO_2$; chloroform-methanol) to afford 1S-5-ethoxy-1-alpha-2-alpha-8,β-trihydroxy-8a-β-octahydroindolizine as a white foam, 370 mg (0.0017 mole; 73% yield). NMR spectral analysis showed the product to be a mixture of isomeric 5-ethoxyswainsonine.

Glycosides of Swainsonine

The invention also includes a one-pot method to convert swainsonine, 1S-8a-beta-octahydroindolizine-1-alpha-2-alpha-8-beta-triol, to its specifically 2-O-glycosylated derivative. These compounds specifically are ether derivatives of swainsonine. Swainsonine glycosides are prepared by the activation of the swainsonine 1,2 diol as its cyclic tin derivative and subsequent reaction with a glycosyl donor. This glycosyl donor is an alkyl halide. The scheme depicting this reaction is illustrated in FIG. 4.

Swainsonine is treated with dibutyltin oxide, or other tin oxides, in an appropriate solvent such as methylene chloride, chloroform, toluene, and the resulting cyclic tin derivative is reacted, in situ, with the glycosyl donor and a catalyst to produce the 2-O-glycosyl derivatized swainsonine. The reactions may be performed while cooling at room temperature, or while heating, but generally require fairly mild conditions. Structural assignments of the swainsonine analogues were made by 1H NMR spectral analysis.

The glycosyl donor is a carbohydrate molecule generally protected at the free hydroxyl groups, and activated at the annomeric centre as a bromide, chloride, fluoride, thioalkyl, trichloroacetamido, or oxazoline derivative. It may be a monosaccharide or oligosaccharide molecule.

The catalyst can include silver salts, mercury salts, thallium salts, either free or bound to an activated support such as alumina, silica gel, or activated molecular sieves; trifluoromethanesulfonic anhydride, crown ethers, etc.

These compounds are expected to have superior binding to alpha-mannosidase II, and therefore, be more potent, and more specific inhibitors of that enzyme. The scheme depicting this reaction is illustrated in FIG. 17.

Examples of the synthesis of glycosyl derivatives of Swainsonine are now described.

EXAMPLE 37

1S-8a-β-octahydroindolizine-1-alpha-8-β-diol-2-alpha-(2-acetamido-2-deoxy-β-D-glucopyrranoside), 40. A mixture of swainsonine (1S-8a-β-octahydroindolizine-1-alpha-2-alpha-8-beta-triol), 0.100 g (0.00058 mole) and 0.160 g (0.00064 mole) dibutyltin oxide, 0.2 g 3/ molecular sieves, and 15 ml chloroform was heated at reflux under argon overnight. The reaction mixture was allowed to cool to room temperature and 350 mg silver silicate on alumina [Chem. Ber., 114 3109 (1981)] was added. The reaction mixture was stirred for about 20 minutes and 0.2.67 g (0.000766 mole; 25% molar excess) chloro 2-acetamido-2-deoxy-3,4,6-tri-O-acetyl-alpha-D-glucopyranose was added. The mixture was stirred under argon overnight. It was then filtered, and concentrated. The residue was then chromatographed on silica gel. The product was eluted with chloroform-methanol to afford 1S-8a-β-octahydroindolizine- 1-alpha-8-β-diol-2-alpha-(2-acetamido-2-deoxy-3,4,6-tri-O-acety-β-D-glucopyranoside) 39, 0.116 g (0.00023 moles; 40%) as a white crystalline solid.

1H NMR (500 Mhz, $CDCl_3$ Z): 5.93 (1H; br); 5.45 (1H; t, J=3.95 Hz); 5.05 (1H; d, J=8.3 Hz); 5.01 (1H; t, J=9.7 Hz); 4.34 (1H; br); 4.29 (1H; br); 4.22 (1H; complex); 4.13 (H; complex); 3.95 (1H; br); 3.78 (1H; complex); 3.65 (1H; br); 3.3 (1H; br); 3.16 (1H; br); 3.0 (1H; br); 2.07 (3H; s); 2.01 (3H; s); 2.00 (3H; s); 1.93 (3H; s); 2.1–1.9 (2H); 1.71 (2H; br).

1S-8a-β-octahydroindolizine-1-alpha-8-β-diol-2-alpha-(2-acetamido-2-deoxy-3,4,6-tri-O-acetyl-β-D-glucopyranoside) 39, 30 mg, was taken up in 5 mL methanol and 0.5 mL of a solution of 0.02 g sodium in 10 mL methanol was added. The solution was allowed to sit for about 2 h. at which point TLC analysis indicated that the reaction had gone to completion. The reaction mixture was filtered through a short column of silica gel in methanol and evaporated to afford 1S-8a-β-octahydroindolizine-1-alpha-8-β-diol-2-alpha-(2-acetamido-2-deoxy-β-D-glucopyranoside), 40, 24 mg as a white crystalline solid.

1H NMR (500 Mhz, $CDCl_3$ Z): 4.45 (1H; d, J=8.45 Hz; H-1 GNAc); 4.30 (1H; complex; H-2 swainsonine); 4.18 (1H; m, H-1 swainsonine; 3.78 (1H; dd, J=2, 12.5 Hz); 3.68–3.60 (2H; complex); 3.60 (1H; t, J=8.5 Hz); 3.43 (1H; t J=8.4 Hz); 3.44–3.30 (2H; complex, containing H-2 GNAc); 2.76–2.73 (2H; H-8a, H-3' swainsonine); 2.48 (1H; dd, J=11.1 Hz, 8.4 Hz, H-3 swainsonine); 1.92 (3H; s, N-Ac), 1.90–1.79 (2H; complex); 1.57 (1H; br d, J=13 Hz); 1.41–1.36 (1H; qt); 1.22–1.07 (1H; qd).

In NOE difference experiments, irradiation at 4.5 ppm (H-1 GNAc), gave a large enhancement at 4.29 ppm (H-2 swainsonine), and also at a multiplet centred at 3.38 (H-2 GNAc). Saturation at 4.29 ppm gave enhancement of the H-1 proton of the N-acetylglucosamine portion of the molecule, as well as enhancement of the peak assigned to H-3 of the swainsonine portion of the molecule.

EXAMPLE 38

1S-8a-β-2-alpha-p-toluoyloxyoctahydroindolizine-1-alpha-8-β-diol, 41. The reaction of 0.100 g (0.0005813 mole) swainsonine, 0.160 g (0.0006394 mole) dibutyltin oxide and 0.497 g (0.003197 mole) p-toluoyl chloride in method using the me: hod described above (see Example 4) afforded 1S-8a-β-2-alpha-p-toluoyloxyoctahydroindolizine-1-alpha-8-β-diol as 25 mg white needles of m.p. 193–197° C. after recrystallization from ethyl acetate.

$^1$H NMR (500 MHz $C_6H_6$ delta): 8.12 (2H; d, J=8.1 Hz); 6.87 (2H; d, J=8.1 Hz); 5.09 (1H; m); 4.37 (1H; m) 3.70 (1H; m); 2.94 (1H; dd, J=1.6, 10.4 Hz); 2.11 (1H; dd, J=7.7, 10.7 Hz); 1.95 (3H; s); 1.83 (2H; complex); 1.50–1.28 (5H; complex); 1.06 (1H; m).

EXAMPLE 39

1S-8a-β-2-alpha-p-nitrobenzoyloxyoctahydroindolizine-1-alpha-8-β-diol, 42. The reaction of 0.100 g (0.0005813 mole) swainsonine, 0.160 g (0.0006394 mole) dibutyltin oxide and 0.594 g (0.003197 mole) p-nitrobenzoyl chloride in methanol using the method described above (see Example 4) afforded 1S-8a-β-2-alpha-p-nitrobenzoyloxyoctahydroindolizine-1-alpha-8-β-diol as 47 mg yellow-orange crystals of m.p. 193°–197° C. (dec.) after recrystallization from ethyl acetate.

$^1$H NMR (500 MHz C$_6$H$_6$ delta): 8.06 (2H; d, J=8.9 Hz); 7.87 (2H; d, J=8.9Hz); 5.23 (1H; m); 4.71 (1H; m); 4.60 (1H; d, J=4.4 Hz); 4.44 (1H; d, J=7.45 Hz); 4.05 (1H; m); 2.76 (1H; br d, J=10.8 Hz); 2.29 (1H; dd, J=7.9, 10.7 Hz); 2.11 (1H; m); 1.97 (1H; m); 1.80 (1H; dd, J=4.0, 8.8 Hz); 1.70 (1H; m); 1.56 (1H; m); 1.45 (1H; m); 1.33 (1H; m).

Assays for Inhibition of N-linked Oligosaccharide Processing

L-PEA Assay: Swainsonine analogues were assayed for their ability to inhibit N-linked oligosaccharide processing using a lectin sensitivity assay. This test also indicates whether the compounds enter tumor cells and measures the degree of toxicity of the compounds for cells. The test is described in J. W. Dennis, Cancer Research 46: 5131, 1986.

Essentially, $2\times10^4$ cells are placed in individual wells of a 96-well microtest plate, wherein the wells contain serial dilutions of the compounds to be tested. After 24 hours, 30 ug/ml of L-PHA is added and the mixture is incubated overnight. DNA synthesis in the cells is then measured by adding 2 uCi of $^3$H-thymidine to each well for 4 hours. The cells are then harvested and the amount of radioactivity incorporated into the host cell DNA is measured in a liquid scintillation counter. The amount of radioactivity present in cells in wells in the absence of L-PHA reflects the toxicity of the test compound and the amount of radioactivity present in the presence of L-PHA reflects the level of inhibition of oligosaccharide processing induced by the test compound. The I$_{50}$ for swainsonine is approximately 20 ng/ml or 0.1 uM. The amount of radioactivity incorporated by cells in the presence of 1S-8 alpha-beta-2-alpha-butyrloxyoctahydroindolizine -1-alpha-8-beta-diol was shown to be comparable to that of swainsonine.

Jack Bean alpha-Mannosidase Assay. Samples of swainsonine and its analogues (100, 30, 10, 3, 1, 0.3 or 0.1 ng) were dissolved in a total volume of 75 ul and transferred into individual wells in a 96 well plate. A volume (37.5 ul) of 0.05M sodium acetate (pH 6.0) was added to each well, followed by 37.5 ul of 0.01M p-nitrophenyl-alpha-D-mannopyanoside, and then 10 ul of a 1: 400 dilution of Jack Bean alpha-mannosidase. After thoroughly shaking to mix, the mixture was incubated at 37° C. for 30 minutes. The reaction was stopped by the addition of 150 ul of 0.5M sodium carbonate (pH 10.0). The absorbance at 405 nm the solution in the wells was determined in an ELISA plate reader.

| Compounds | D$_{50}$ Values (Inhibition) | |
|---|---|---|
| | L-PHA assay (ng/ml) | J.B. mannosidase (μg/mL) |
| swainsonine | 33 | 0.07 |
| 5 | 500 | 70 |
| 6 | 66 | 35 |
| 23 | >>1,000 | 10 |
| 3 | 66 | 35 |
| 42 | 66 | 35 |
| 41 | 1,000 | 100 |
| Kefunensine[a] | 1,000 | 35 |

[a]M. Hasimoto et a.J. Org. Chem. 54: 4015 (1989)

Assay for Bone Marrow Call Proliferation Induced by Swainsonine Analogues. Pathogen-free C$_{57}$BL/6 mice at 8–14 weeks of age were quarantined for one week prior to their use in the experiments described below. Mice were inoculated intraperitoneally twice daily with a designated dose of swainsonine or an analogue of swainsonine for a period of four days. Eighteen hours following the last injection, the mice were sacrificed, bone marrow cells were obtained using standard technology (S. C. White et el., J. Natl.Cancer Inst. 83 1125, 1991). Cellularity of the bone marrow cells so obtained was determined by directly counting the cells after they were flushed from the femurs and tibia of the mice. The cells were processed according to the procedure described in the GIBCO-BRL Mouse Bone Stem Cell Proliferation Kit, and the number of colony forming units (CFU) was assessed using the procedures also described in the kit. For kinetic experiments, mice were administered 10 ug of the analogue (this was the optimum dose in all cases) twice daily for the designated number of days. The experiments were designed so that all regimens terminated on the same day. Eighteen hours after the last injection, the mice were sacrificed and bone marrow cells were obtained and processed as described above.

| | Dose Dependent Effect of Analogues On in vivo CFU Formation and On in vivo Bone Marrow Cellularity: | | | | |
|---|---|---|---|---|---|
| Compound | Doses of Drug (μg, twice daily i.p.) | Mean of CFU Formation | | Mean of Cellularity ($\times 10^7$) | |
| | | Expt. 1 | Expt. 2 | Expt. 1 | Expt. 2 |
| 36 | Control | 155 | | 1.59 | |
| | 5 | 291 | | 2.28 | |
| | 10 | 545 | | 5.27 | |
| | 20 | 327 | | 2.59 | |
| swainsonine | 10 | 550 | | 5.86 | |
| 6 | Control | 140 | | 1.83 | |
| | 5 | 200 | | 2.57 | |
| | 10 | 437 | | 3.83 | |
| | 20 | 295 | | 2.73 | |
| 5 | Control | 136 | | 1.82 | 1.64 |
| | 5 | 200 | | 2.91 | 3.33 |
| | 10 | 324 | | 5.76 | 4.76 |
| | 20 | 293 | | 3.07 | 3.38 |
| | 40 | 287 | | 3.07 | |
| swainsonine | 10 | | | | 5.76 |
| 41 | Control | 137 | 1.20 | | |
| | 5 | 195 | 2.22 | | |
| | 10 | 359 | 2.99 | | |
| | 20 | 214 | 2.14 | | |
| swainsonine | 10 | 446 | 3.73 | | |
| 42 | Control | 137 | 1.20 | | |
| | 5 | 213 | 2.68 | | |
| | 10 | 373 | 3.21 | | |
| | 20 | 242 | 2.63 | | |
| swainsonine | 10 | 446 | 3.73 | | |

| | Time Course Effect of Swainsonine Analogue (10 μg) on CFU Formation (in vivo): | | | | |
|---|---|---|---|---|---|
| Compound | Days of Drug Treatment μg, twice daily i/p.) | Mean of CFU Formation | | Mean of Cellularity ($\times 10^7$) | |
| | | Cpd | Ctrl | Cpd | Ctrl |
| 6 | 1 | 250 | 145 | 3.56 | 1.37 |
| | 2 | 432 | 145 | 4.63 | 1.69 |
| | 3 | 550 | 145 | 5.88 | 1.69 |
| | 4 | 618 | 145 | 7.63 | 1.75 |
| | 5 | 614 | 145 | 6.25 | 1.69 |
| | 6 | 488 | 145 | 5.38 | 1.50 |
| 5 | 1 | 250 | 150 | 3.00 | 1.35 |
| | 2 | 436 | 150 | 4.18 | 1.35 |
| | 3 | 568 | 150 | 5.59 | 1.35 |

-continued

| | | | | |
|---|---|---|---|---|
| 4 | 623 | 150 | 7.42 | 1.35 |
| 5 | 621 | 150 | 6.88 | 1.35 |
| 6 | 518 | 150 | 5.24 | 1.35 |

Summary of Experiments Testing the Effect of Swainsonine Analogues on Bone Marrow Cellularity and CFU Formation:

| Compound | Times Tested | Results |
|---|---|---|
| 6 | 3 | Stimulates CFU and cellularity but not approximating swainsonine. (Swainsonine was not run in these experiments) |
| 5 | 2 | Stimulates CFU & cellularity but not approximating swainsonine. (Swainsonine was not run in these experiments) |
| 3 | 1 | 10 μg optimal dose and comparable to 10 μg swainsonine |
| 23 | 1 | 10 μg optimal dose and comparable to 10 μg swainsonine |
| 41 | 1 | Stimulates CFU & cellularity but not approximating swainsonine. |
| 42 | 1 | Stimulates CFU & cellularity but not approximating swainsonine. |

The Compounds of FIG. 3

1 Swainsonine (1S-8a-β-octahydroindolizine-1-alpha-2-alpha-8-β-triol)

4 1S-8a-β-2-alpha-trimethylsilyloxyoctahydroindolizine-1-alpha-8-β-diol 7 1S-8a-β-2-alpha-succinyloxyoctahydroindolizine-1-alpha-8-β-diol 5 1S-8a-β-2-alpha-benzoyloxyoctahydroindolizine-1-alpha-8-β-diol 41 1S-8a-β-2-alpha-p-toluoyloxyoctahydroindolizine-1-alpha 8-β-diol 42 1S-8a-β-2-alpha-p-nitorbenzoyloxyoctahydroindolizine-1-alpha-8-D-diol 6 1S-8a-β-2-alpha-octanoyloxyoctahydroindolizine-1-alpha-8-β-diol 3 1S-8a-β-2-alpha-butanoyloxyoctahydroindolizine-1-alpha-8-β-diol 12 (1S,2R,8R,8aR)-1,2,8-trihydroxy-1,2,3,5,8,8a-hexahydro-5-oxyindolizine 6

13 (1S,2R,8R,8aR)-1,2,8-triacetoxy-1,2,3,5,8,8a-hexahydro-5-oxyindolizine 7

23 7-ethoxy-(1S,2R,8R,8aR)-1,2,8-trihydroxy-octahydro-5-oxyindolizine 25 7-ethoxy-(1S,2R,8R,8aR)-1,2,8-trihydroxyocahydroindolizine (7-ethoxyswainsonine)

26 1S-7-β-bromo-1-alpha-2-alpha-6-alpha-8β-tetraacetoxy-8a-β-octahydro-5-oxyindolizine 27 1S-6-β-bromo-1-alpha-2-alpha-7-alpha-8β-tetraacetoxy-8a-β-octahydro-5-oxyindolizine 28 1S-7-β-bromo-1-alpha-2-alpha-6-alpha-8β-tetrahydroxy-8a-β-octahydroindolizine 29 1S-1-alpha-2-alpha-6-alpha-8β-tetra-O-acetyl-8a-β-octahydro-5-oxyindolizine 31 1S-1-alpha-2-alpha-6-alpha-8β-tetrahydroxy-8a-β-octahydroindolizine 30 1S-1-alpha-2-alpha-7-alpha-8β-tetra-O-acetyl-8a-β-octahydro-5-oxyindolizine 32 1S-6-alpha,7β-dibromo-1-alpha-2-alpha-8β-tri-O-acetyl-8a-β-octahydro-5-oxyindolizine 33 1S-6-alpha,7β-dibromo-1-alpha-2-alpha-8β-trihydroxy-8a-β-octahydroindolizine 34 1S-6β, 7β-dihydroxy-1-alpha-2-alpha-8β-tri-O-acetyl-8a-β-octahydro-5-oxyindolizine 35 1S-1-alpha-2-alpha-6β,7β-8β-penta-O-acetyl-8a-β-octahydro-5-oxyindolizine 36 1S-1-alpha-2-alpha-6β,7β-8β-pentahydroxy-8a-β-octahydroindolizine 37 1S-1-alpha-2-alpha-8β-trihydroxy-8a-β-octa-5-oxyhydroindolizine 38 1S-5-ethoxy-1-alpha-2-alpha-8β-trihydroxy-8a-β-octahydroindolizine 40 1S-8a-β-octahydroindolizine-1-alpha-8-β-diol-2-alpha-(2-acetamido-2-deoxy-β-D-glucopyranoside)

39 1S-8a-β-octahydroindolizine-1-alpha-8-β-diol-2-alpha-(2-acetamido-2-deoxy-3,4,6-tri-O-acetyl-β-D-glucopyranoside).

The embodiments of the invention in which an exclusive property or privilege is claimed are as follows:

1. A method of making an analog of swainsonine comprising the steps of treating swainsonine with dialkyltin oxide in a solvent to yield a cyclic tin derivative, reacting said tin derivative with an agent selected from the group consisting of an acylating agent, a protecting agent and an alkylating agent to result in an analog of swainsonine which is selectively derivatized at the C2 hydroxyl group, wherein when a protecting agent is employed, said protecting agent forms a protected compound with hydroxyl groups at the 1 and 8 positions and said protected compound is subsequently derivatized at the C2 hydroxyl group by reacting said protected compound with an alkylating or acylating agent and then removing the protecting groups therefrom by hydrolysis or hydrogenolysis.

2. A method of claim 1 wherein said solvent is selected from the group consisting of methylene chloride, chloroform, toluene and methanol.

3. A method of claim 1 wherein said acylating agent is selected from the group consisting of activated carboxylic acids, including acid halides, acid anhydrides, activated amides, activated esters, sulfonic acid esters, fatty acid groups, aromatic acyl groups, and heterocyclic acyl groups.

4. A method of claim 1 wherein said protecting agent is selected from the group consisting of benzyl chloride, allyl chloride, triphenylmethyl chloride, 4-methoxytrityl chloride, chlorotrimethyl-silane, t-butylchlorodimethsilane, and t-butyldiphenylchlorosilane.

5. A method of claim 1 wherein said alkylating agent is an alkyl halide.

6. A method of claim 1 wherein said alkylating agent is a glycosylating agent.

* * * * *